United States Patent
Grant et al.

(10) Patent No.: US 11,110,151 B2
(45) Date of Patent: Sep. 7, 2021

(54) COMPOSITION AND METHOD FOR REDUCING HYPOGLYCEMIA EVENTS IN DIABETES TREATMENT

(71) Applicant: MannKind Corporation, Westlake Village, CA (US)

(72) Inventors: Marshall Grant, Newtown, CT (US); Simon R. Bruce, San Diego, CA (US); Robert A. Baughman, Brookfield, CT (US)

(73) Assignee: MannKind Corporation, Westlake Village, CA (US)

( * ) Notice: Subject to any disclaimer, the term of this patent is extended or adjusted under 35 U.S.C. 154(b) by 0 days.

(21) Appl. No.: 16/449,308

(22) Filed: Jun. 21, 2019

(65) Prior Publication Data

US 2019/0365866 A1 Dec. 5, 2019

Related U.S. Application Data

(60) Continuation-in-part of application No. 15/910,876, filed on Mar. 2, 2018, now Pat. No. 10,857,207, which is a division of application No. 14/102,383, filed on Dec. 10, 2013, now Pat. No. 9,943,571, which is a continuation of application No. 13/351,855, filed on Jan. 17, 2012, now Pat. No. 8,623,817, which is a division of application No. 12/539,459, filed on Aug. 11, 2009, now Pat. No. 8,119,593.

(60) Provisional application No. 61/138,863, filed on Dec. 18, 2008, provisional application No. 61/097,495, filed on Sep. 16, 2008, provisional application No. 61/097,516, filed on Sep. 16, 2008, provisional application No. 61/087,943, filed on Aug. 11, 2008, provisional application No. 62/688,670, filed on Jun. 22, 2018.

(51) Int. Cl.
*A61K 38/28* (2006.01)
*A61K 9/00* (2006.01)
*A61K 47/54* (2017.01)

(52) U.S. Cl.
CPC ............ *A61K 38/28* (2013.01); *A61K 9/0021* (2013.01); *A61K 9/0075* (2013.01); *A61K 47/545* (2017.08)

(58) Field of Classification Search
CPC .............................. A61K 38/28; A61K 9/0075
See application file for complete search history.

(56) References Cited

U.S. PATENT DOCUMENTS

| | | | | |
|---|---|---|---|---|
| 2003/0017211 A1* | 1/2003 | Steiner | ................ | A61K 9/5146 424/499 |
| 2005/0153874 A1* | 7/2005 | Cheatham | ................ | A61P 3/10 514/1.9 |
| 2006/0153778 A1* | 7/2006 | Gelber | ................ | A61K 31/495 424/46 |
| 2006/0239934 A1* | 10/2006 | Cheatham | ............ | A61K 9/0073 424/46 |

OTHER PUBLICATIONS

Technosphere Inhaled Insulin (AFREZZA), M. Rendell, Creighton University Diabetes Center, Omaha, Nebraska, USA Drugs of Today 2014, 50(12):813-827.

* cited by examiner

*Primary Examiner* — Gyan Chandra
(74) *Attorney, Agent, or Firm* — Withers Bergman LLP; Alan D Gardner

(57) ABSTRACT

An ultra-rapid acting insulin composition and method for treating hyperglycemia in patients with diabetes are disclose. The composition is an inhalable dry powder composition comprising fumaryl diketopiperazine and insulin for pulmonary delivery, which significantly reduces the rates of hypoglycemic events in patients in patients on mealtime insulin therapy.

12 Claims, 4 Drawing Sheets

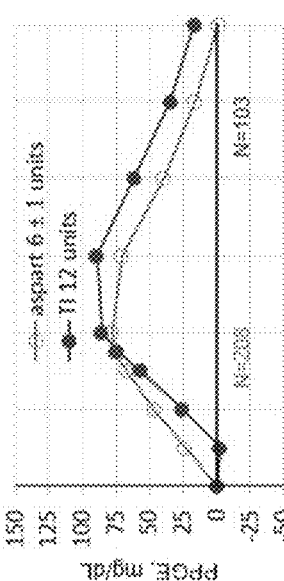
FIG. 3C
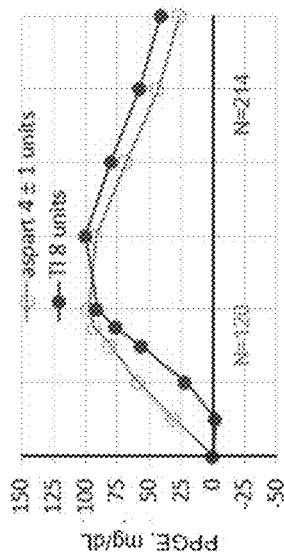
FIG. 3B
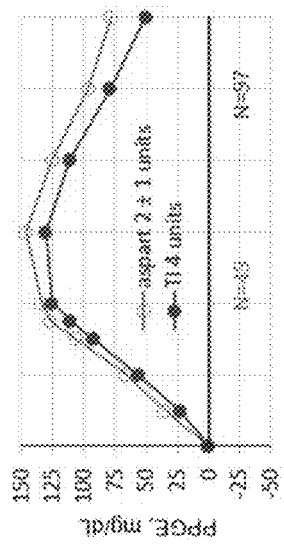
FIG. 3A
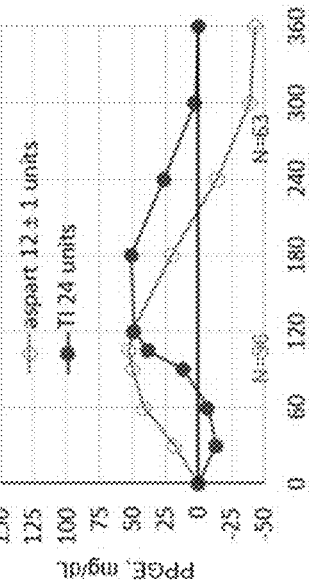
FIG. 3F
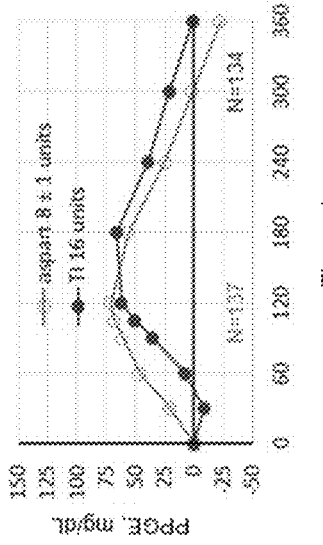
FIG. 3E
FIG. 3D

COMPOSITION AND METHOD FOR REDUCING HYPOGLYCEMIA EVENTS IN DIABETES TREATMENT

CROSS REFERENCE TO RELATED APPLICATIONS

This application is a continuation-in-part of U.S. patent application Ser. No. 15/910,876, filed on Mar. 2, 2018, which is a divisional of U.S. patent application Ser. No. 14/102,383, filed on Dec. 10, 2013, now U.S. Pat. No. 9,943,571, which is a continuation of U.S. patent application Ser. No. 13/351,855, filed on Jan. 17, 2012, now U.S. Pat. No. 8,623,817, which is a divisional of U.S. patent application Ser. No. 12/539,459, filed on Aug. 11, 2009, now U.S. Pat. No. 8,119,593, which claims benefit of priority under 35 U.S.C. § 119(e) from U.S. Provisional Patent Application Ser. Nos. 61/087,943 filed Aug. 11, 2008, 61/097,495 filed Sep. 16, 2008, 61/097,516 filed Sep. 16, 2008, and 61/138,863 filed Dec. 18, 2008, the contents of each of these applications are incorporated herein by reference in their entirety.

This application claims the benefit under 35 U.S.C. § 119(e) from U.S. Provisional Patent Application Ser. No. 62/688,670, filed on Jun. 22, 2018, the entire content of which is incorporated herein by reference.

TECHNICAL FIELD

Compositions and methods for treating diabetes are disclosed. The compositions are effective in reducing the rates of hypoglycemic events in patients in mealtime insulin therapy and comprise and inhalable insulin comprising a diketopiperazine composition for pulmonary delivery.

BACKGROUND

Diabetes mellitus (hereinafter, diabetes) currently afflicts at least 200 million people worldwide. The two main subtypes of diabetes include types 1 and type 2. Type 1 accounts for about 10% of those afflicted with diabetes. Type 1 diabetes is caused by autoimmune destruction of insulin-secreting β-cells in the pancreatic islets of Langerhans. Type 2 diabetes accounts for the remaining 90% of individuals afflicted, and the prevalence is increasing. Type 2 diabetes is often, but not always, associated with obesity, and although previously termed late-onset or adult-onset diabetes, is now becoming increasingly more prevalent in younger individuals. Type 2 diabetes is caused by a combination of insulin resistance and inadequate insulin secretion.

In a non-stressed, non-diabetic individual, the basal glucose level will tend to remain the same from day to day because of an intrinsic feedback loop. Any tendency for the plasma glucose concentration to increase is counterbalanced by an increase in insulin secretion and a suppression of glucagon secretion, which regulate hepatic glucose production (gluconeogenesis and release from glycogen stores) and tissue glucose uptake to keep the plasma glucose concentration constant. If the individual gains weight or becomes insulin resistant for any other reason, blood glucose levels will increase, resulting in increased insulin secretion to compensate for the insulin resistance. Therefore the glucose and insulin levels are modulated to minimize changes in these concentrations while relatively normal production and utilization of glucose are maintained.

Five different phases of insulin secretion have been identified: (1) basal insulin secretion wherein insulin is released in the post-absorptive state; (2) the cephalic phase wherein insulin secretion is triggered by the sight, smell and taste of food, before any nutrient is absorbed by the gut, mediated by pancreatic innervation; (3) early-phase insulin secretion wherein an initial burst of insulin is released within the first 5-10 minutes after the β-cell is exposed to a rapid increase in glucose, or other secretagogues; (4) second-phase insulin secretion wherein the insulin levels rise more gradually and are related to the degree and duration of the stimulus; and (5) a third-phase of insulin secretion that has only been described in vitro. During these stages, insulin is secreted, like many other hormones, in a pulsatile fashion, resulting in oscillatory concentrations in the blood. Oscillations include rapid pulses (occurring every 8-15 minutes) superimposed on slower oscillations (occurring every 80-120 minutes) that are related to fluctuations in blood glucose concentration.

Insulin secretion can be induced by other energetic substrates besides glucose (particularly amino acids) as well as by hormones and drugs. Of note is that the insulin response observed after food ingestion cannot be accounted for solely by the increase in blood glucose levels, but also depends on other factors such as the presence of free fatty acids and other secretagogues in the meal, the neural-activated cephalic phase and gastrointestinal hormones.

When an individual is given an intravenous glucose challenge, a biphasic insulin response is seen which includes a rapid increase with a peak, an interpeak nadir and a subsequent slower increasing phase. This biphasic response is only seen when glucose concentration increases rapidly, such as after a glucose bolus or glucose infusion. A slower increase in glucose administration, what is seen under physiologic conditions, induces a more gradually increasing insulin secretion without the well-defined biphasic response seen in response to bolus infusion of glucose.

Modeling of early-phase insulin responses under normal physiologic conditions has demonstrated that, after a meal, glucose concentration increases more gradually ($C_{max}$ reached in approximately 20 minutes) than seen with intravenous bolus injections of glucose ($C_{max}$ reached in approximately 3-10 minutes).

Healthy pancreatic β-cells generate an early response to a meal-like glucose exposure that rapidly elevates serum insulin both in the portal circulation and in the periphery. Conversely, defective β-cells, which have an impaired early-phase insulin response, generate a sluggish response to the meal-like glucose exposure.

Increasingly, evidence indicates that an early relatively rapid insulin response following glucose ingestion plays a critical role in the maintenance of postprandial glucose homeostasis. An early surge in insulin concentration can limit initial glucose excursions, mainly through the inhibition of endogenous glucose production. Therefore the induction of a rapid insulin response in a diabetic individual is expected to produce improved blood glucose homeostasis.

In a non-diabetic individual, a meal induces the secretion of a burst of insulin, generating a relatively rapid spike in serum insulin concentration that then decays relatively quickly (see FIG. 1). This early-phase insulin response is responsible for the shut-off, or reduction, of glucose release from the liver. Homeostatic mechanisms then match insulin secretion (and serum insulin levels) to the glucose load. This is observed as a slow decay of modestly elevated serum insulin levels back to baseline and is second-phase kinetics.

A central characteristic of diabetes is impaired β-cell function. One abnormality that occurs early in the disease progression in both type 1 and 2 diabetes is the loss of eating-induced rapid insulin response. Consequently, the liver continues to produce glucose, which adds to the glucose that is ingested and absorbed from the basic components of a meal.

Type 2 diabetics typically exhibit a delayed response to increases in blood glucose levels. While non-diabetic individuals usually begin to release insulin within 2-3 minutes following the consumption of food, type 2 diabetics may not secrete endogenous insulin until blood glucose begins to rise, and then with second-phase kinetics, that is a slow rise to an extended plateau in concentration. As a result, endogenous glucose production is not shut off and continues after consumption and the patient experiences hyperglycemia (elevated blood glucose levels). Another characteristic of type 2 diabetes is impaired insulin action, termed insulin resistance. Insulin resistance manifests itself as both a reduced maximal glucose elimination rate ($GER_{max}$) and an increased insulin concentration required to attain $GER_{max}$. Thus, to handle a given glucose load more insulin is required and that increased insulin concentration must be maintained for a longer period of time. Consequently, the diabetic patient is also exposed to elevated glucose concentrations for prolonged periods of time, which further exacerbates insulin resistance. Additionally, prolonged elevated blood glucose levels are themselves toxic to β-cells.

Type 1 diabetes occurs as a result of the destruction of the insulin-producing cells of the pancreas (β-cells) by the body's own immune system. This ultimately results in a complete insulin hormone deficiency. Type 2 diabetes arises from different and less well understood circumstances. The early loss of early phase insulin release, and consequent continual glucose release, contributes to elevated glucose concentrations. High glucose levels promote insulin resistance, and insulin resistance generates prolonged elevations of serum glucose concentration. This situation can lead to a self-amplifying cycle in which ever greater concentrations of insulin are less effective at controlling blood glucose levels. Moreover, as noted above, elevated glucose levels are toxic to the β-cells, reducing the number of functional β-cells. Genetic defects impairing the growth or maintenance of the microvasculature nourishing the islets can also play a role in their deterioration (Clee, S. M., et al. Nature Genetics 38:688-693, 2006). Eventually, the pancreas becomes overwhelmed, and individuals progress to develop insulin deficiency similar to people with type 1 diabetes.

Insulin therapy is the standard treatment for type 1 diabetes. While incipient type 2 diabetes can be treated with diet and exercise, most early stage type 2 diabetics are currently treated with oral antidiabetic agents, but with limited success. Patients generally transition to insulin therapy as the disease progresses. These treatments, however, do not represent a cure.

In a typical progression the first oral antidiabetic agent used is metformin, a suppressor of hepatic glucose output. Use of metformin is not associated with weight gain or hypoglycemia. If metformin treatment is insufficient to control hyperglycemia, an insulin secretagogue, most typically a sulfonylurea, can be added to the treatment regimen. Secretagogues raise the basal level of insulin in order to lower average blood glucose levels. Use of sulphonylureas is associated with weight gain and can lead to hypoglycemia, although severe hypoglycemia is infrequent. If this combination of two oral antidiabetic agents is inadequate to control hyperglycemia either a third oral agent, such as a glitazone, or a long-acting, basal insulin can be added to the regimen. As the disease progresses, insulin therapy can be intensified by the addition of intermediate and short (rapid) acting insulin preparations administered in association with at least some of the day's meals.

Current insulin therapy modalities can supplement or replace endogenously-produced insulin to provide basal and second-phase-like profiles but do not mimic early-phase kinetics (see FIG. 2). Additionally, conventional insulin therapy often involves only one or two daily injections of insulin. However, more intensive therapy such as three or more administrations a day, providing better control of blood glucose levels, are clearly beneficial (see for example Nathan, D. M., et al., N. Engl. J. Med 353:2643-53, 2005), but many patients are reluctant to accept the additional injections. Use of these conventional insulin preparations is associated with weight gain and a significant risk of hypoglycemia including severe, life-threatening hypoglycemic events.

Until recently, subcutaneous (SC) injection has been the only route of delivering insulin for self-administration by patients. However, SC insulin administration does not lead to optimal pharmacodynamics for the administered insulin. Absorption into the blood of the insulin, including, rapid acting insulin analogues, does not mimic the prandial physiologic insulin secretion pattern of a rapid spike in serum insulin concentration. Subcutaneous injections are also rarely ideal in providing insulin to type 2 diabetics and may actually worsen insulin action because of delayed, variable and slow rate of absorption into the bloodstream. It has been shown, however, that if insulin is administered intravenously with a meal, early stage type 2 diabetics experience the shutdown of hepatic glucose release and exhibit increased physiologic glucose control of their sugar levels. In addition, their free fatty acids levels fall at a faster rate than without insulin therapy. While possibly effective in treating type 2 diabetes, intravenous administration of insulin is not a reasonable or daily adequate therapy, as it is not safe or feasible for patients to intravenously administer insulin at every meal.

For a short period of time there was an inhalable insulin, Exubera® (Pfizer), which was marketed for the treatment of diabetes. This insulin preparation had a pharmacokinetic profile similar to the injectable rapid acting analogues and was used as a substitute for short acting insulin in the standard treatment paradigm. While this insulin preparation did allow patients using short acting insulins to avoid injections, it offered no other notable advantage which contributed to its commercial failure. Moreover, because its kinetic profile was so similar to subcutaneously administered regular insulin and rapid-acting insulins, that after accounting for differences in bioavailability, dosing and modes of administration could generally follow that of those subcutaneous insulins.

Low blood sugar or hypoglycemia is when the levels of sugar drop in a patient below 70 mg/dL and the patient exhibits various symptoms, including, confusion, dizziness, feeling shaky, hunger, headaches, pounding heart/raising pulse, pale skin, sweating, trembling, weakness, and anxiety. Severe symptoms include, poor coordination, poor concentration, numbness in mouth and tongue, passing out, seizures, nightmares, and coma. Hypoglycemia results frequently in people with diabetes, and particularly, in patients undergoing insulin therapy (too much insulin that peaks late), or therapy with sulfonylureas, such as repaglinide, glimepiride and glipizide. The incidence of hypoglycemia in patients treated with insulin can be very severe and can lead to coma and possibly death if not promptly attended. Thus, people in insulin therapy must be vigilant in controlling their sugars, however, hypoglycemia is prevalent and a condition of current insulin therapy.

While diabetes is managed reasonably well in many patients, many of the patients and in particular, patients with type 1 diabetes using rapid acting analogs at mealtime, the patients suffer with severe hypoglycemic events regularly. Accordingly, there is a need to improve glycemic control in order to minimize hypoglycemic episodes when treating hyperglycemia. Such methods are the object of the present disclosure.

SUMMARY OF THE INVENTION

Embodiments disclosed herein include methods useful for treating diabetes mellitus including both type 1 and type 2 using an ultra-rapid, ultra-fast acting insulin formulation which reduces hypoglycemic episodes when administered to patients.

The methods comprise administering to a patient experiencing hypoglycemia and in insulin therapy, a dose of an inhalable ultra-fast acting insulin to reduce hypoglycemic episodes in the patient. In one embodiment, the patient is administered a dry powder dose of an insulin composition comprising insulin and a diketopiperazine, including, fumaryl diketopiperazine in amounts of 4 units, 8 units, 12 units and 16 units dosages per inhalation, or combinations thereof as required by the patient.

In an exemplary embodiment, the inhalable ultra-fast or rapid acting insulin composition is administered at the beginning of the meal and at a subsequent point in time. In certain embodiments, the ultra-fast insulin composition is insulin-FDKP and is administered by pulmonary inhalation. For example, a patient can be administered up to 90 units or more on an ultra-rapid formulation by inhalation using a dry powder inhaler. Such formulations can be advantageously used in the treatment of patients with subcutaneous insulin resistance, and methods of selecting such patients are also disclosed herein.

Embodiments of the method include administration of insulin in a manner that mimics the meal-related early phase insulin response. In mimicking early phase kinetics peak serum insulin levels can be reached within about 12 to within about 30 minutes after administration. Serum levels can also return to approach baseline within about two or three hours of administration. Insulin preparations mimicking early phase kinetics in this manner are referred to herein as ultra-rapid acting insulins. In one embodiment a dose sufficient to reduce or control glucose excursions is used. In one embodiment, insulin is administered to a patient in need of insulin therapy at mealtime, that is, within about 10 minutes, preferably 5 minutes before, or 30, 25, 15, or 10 minutes after starting a meal. (The shorter times after starting a meal being preferred for patients with normal gastric emptying, the longer times after starting a meal being appropriate for patients with delayed gastric emptying).

In further embodiments, glycemic control during a meal to prevent hypoglycemia can be achieved by administering an ultra-rapid insulin formulation at least twice during the meal period, wherein the patient is administered an insulin dose at the beginning of the meal (that is within 10 minutes plus or minus of starting a meal), followed by a second or supplemental dose at about 30 to 120 minutes after beginning the meal. Blood glucose levels can be tested or monitored with a continuous glucose monitoring device up to about 120 minutes to ascertain that a third dose is not necessary depending on the carbohydrate load consumed. In this embodiment, blood glucose levels can be controlled more effectively by providing the necessary ultra-rapid acting insulin dosage in specified intervals to spread out the insulin effect so as not to cause hypoglycemia and maintain the glucose level within acceptable range. In one embodiment, the ultra-rapid acting insulin comprises a crystalline dry powder composition for oral inhalation comprising insulin and fumaryl diketopiperazine. In this embodiment, patients who frequently experience hypoglycemia and/or fear hypoglycemia events can decrease or prevent hypoglycemia episodes by substituting injectable insulin therapy with orally inhalable insulin therapy to achieve their glycemic targets.

In one embodiment, a method for reducing hypoglycemic events in a patient with diabetes mellitus and undergoing insulin therapy is provided. The method comprises, providing a combination therapy to the patient, which comprises administering a basal, or longer-acting insulin, including, insulin glargine, insulin detemir, insulin degludec, and the like once daily to a patient in need of treatment, and administering an ultra-short-acting, ultra-rapid acting insulin at mealtime to regulate blood sugar levels by maintaining the levels at an acceptable range upon food intake between meals and thereby preventing hypoglycemia.

In another embodiment, a method of controlling glucose levels after a meal and reducing the risks of hypoglycemia in a patient in insulin therapy, comprising administering an ultra-fast acting insulin at mealtime to improve early post-meal glucose control and limit the risk of post-meal hypoglycemia. In one embodiment, an initial dosage of an ultra-rapid acting insulin is administered to a diabetic patient at mealtime, or just prior to eating a meal, including a snack, followed by administering a supplemental dose of the ultra-rapid acting insulin if blood glucose levels remain at >140 mg/dL upon testing 120 minutes after the meal is consumed.

In another embodiment, a method to lower the rates of hypoglycemia in a patient with diabetes and undergoing injectable rapid acting insulin analog therapy comprises discontinuing the injectable rapid acting insulin therapy and administering an inhalable ultra-rapid acting insulin composition comprising a fumaryl diketopiperazine dry powder comprising a recombinant human insulin, wherein the inhalable ultra-rapid acting insulin composition reduces the rates of hypoglycemia episodes up to 2 to 5 hours after meals. In a particular embodiment, the ultra-rapid acting insulin reduces severe hypoglycemia rates on average about 30% of the time in patients achieving HbA1c<7.0%, wherein the incidence of severe hypoglycemia was lower in patients administered ultra-rapid acting insulin patients comprising fumaryl diketopiperazine when compared to patients receiving a subcutaneous injection of a rapid acting analog including insulin aspart averaging about 18%.

In one embodiment, a method of treatment comprises a dry powder composition and methods for using the compositions in the treatment of diabetes mellitus. The composition is provided in a dry powder inhaler comprising a replaceable cartridge comprising a dry powder for inhalation for delivery to the lungs for local or systemic delivery into the pulmonary circulation. The dry powder inhaler is a breath-powered inhaler which is compact, reusable or disposable, has various shapes and sizes, and comprises a system of airflow conduit pathways for the effective and rapid delivery of powder medicament to the lungs and the systemic circulation.

In a particular embodiment, the method of treating diabetes mellitus utilizes a dry powder drug delivery system which is designed for drug delivery to the lungs, including by oral inhalation, for rapid delivery and onset of insulin action to target tissues using the arterial circulation in the lungs. In this method, the insulin can reach its target site in a therapeutically effective manner.

In another embodiment, the method comprises administering a stable pharmaceutical composition comprising, an ultra-rapid or ultra-fast acting insulin, or an analog thereof, for example, recombinant human insulin for treating diabetes type 1 and type 2, and delivering the insulin into the systemic circulation of a subject by pulmonary inhalation using a high resistance to airflow dry powder inhaler which can comprise a capsule or a cartridge containing the composition. In one embodiment, the method comprises providing to a patient in need of treatment the dry powder inhaler comprising the recombinant human insulin in a stable dry powder formulation, and administering the insulin by oral inhalation.

In one embodiment, the drug delivery system comprises a dry powder inhaler comprising a diketopiperazine-based drug formulation for delivering the ultra-rapid acting insulin, or analogs thereof including, a recombinant human insulin-fumaryl diketopiperazine formulation. The method provides advantages over typical methods of drug delivery, such as, oral tablet and subcutaneous and intravenous injectable/infusion drug products that are sensitive to degradation and/or enzymatic deactivation upon contact with local tissue or venous blood after being delivered by injection.

In an exemplary embodiment, the method for preventing or reducing severe hypoglycemia comprises, providing a dry powder inhaler to a patient undergoing mealtime injectable insulin analog therapy with injectable insulin aspart, insulin lispro or insulin glulisine, wherein the patient experiences recurrent severe hypoglycemia episodes resulting from excessive rapid acting injectable insulin analogs administration, and replacing the injectable insulin analog therapy by administering an effective amount of an ultra-rapid/fast-acting insulin composition comprising an inhalable dry powder comprising insulin and fumaryl diketopiperazine at mealtime, followed by a supplemental dose of the ultra-rapid/fast-acting insulin composition if necessary after 120 minutes post-meal to decrease the hypoglycemic episodes in the patient. In one embodiment, the inhalable ultra-fast or ultra-rapid acting insulin reduces the hypoglycemic episodes in a patient by up to 30% when compared to the injectable rapid acting insulin anolog therapy at mealtime.

In another embodiment, a dry powder comprising insulin and fumaryl diketopiperazine can also be administered as a part of up-front combination therapy with an oral agent or tablet. In a particular embodiment, an inhalable dry powder comprising insulin adsorbed onto fumaryl diketopiperazine crystalline particles may also be administered instead of administering a rapid acting injectable insulin at mealtime. The orally inhalable insulin powder can reduce severe hypoglycemic episodes in the diabetic patient, or reduce severe hypoglycemic events associated with injectable rapid acting insulin analogs therapy.

In another embodiment, the oral inhalation system comprises a breath-powered dry powder inhaler, a capsule or a cartridge containing a dry powder for delivering to the pulmonary tract and lungs, including the insulin medicament. In one embodiment, the medicament can comprise, for example, a drug formulation for pulmonary delivery comprising pharmaceutically acceptable carriers and excipients, for example, a composition comprising a diketopiperazine in a crystalline form that self-assemble in a suspension, an amorphous form, and/or a microcrystalline form comprising crystallites that do not self-assemble in suspension, or combinations thereof, and an insulin or an insulin analog. In alternate embodiments, the dry powder may be formulated comprising other or additional carriers and/or excipients other than diketopiperazines, for example a sugar, including trehalose, an amino acid, including, leucine or isoleucine, a salt of a mild acid such as citrate or tartrate, and the insulin or the insulin analog thereof.

BRIEF DESCRIPTION OF THE DRAWINGS

FIG. 3A-3F depict graphic representation of data obtained from 52-week clinical study in type 1 diabetes patients treated with the instant ultra-rapid acting insulin (TI, 652 glucose profiles in 264 individuals; closed circles) compared to a rapid acting insulin analog, insulin aspart (674 glucose profiles in 261 individuals; open circles). Post-prandial glucose was represented as the average glucose levels of the number of patients treated and monitored for a period of 360 minutes. The data show the post-prandial glucose excursion (PPGE) profiles of patients (N) treated with either insulin aspart or TI for various insulin dosages tested. That is, in FIG. 3A, 4 units of TI were used to treat 97 patients, compared to 49 patients treated with 2±1 insulin aspart; in FIG. 3B, 8 units of TI compared to 4±1 units of insulin aspart; in FIG. 3C, 12 units of TI were compared to 6±1 units of insulin aspart; in FIG. 3D, 16 units of TI were compared to 8±1 units of insulin aspart; in FIG. 3E, 20 units of TI were compared to 10±1 units of insulin aspart; and in FIG. 3F, 24 units of TI were compared to 12±1 units of insulin aspart.

DEFINITION OF TERMS

Figure 1:
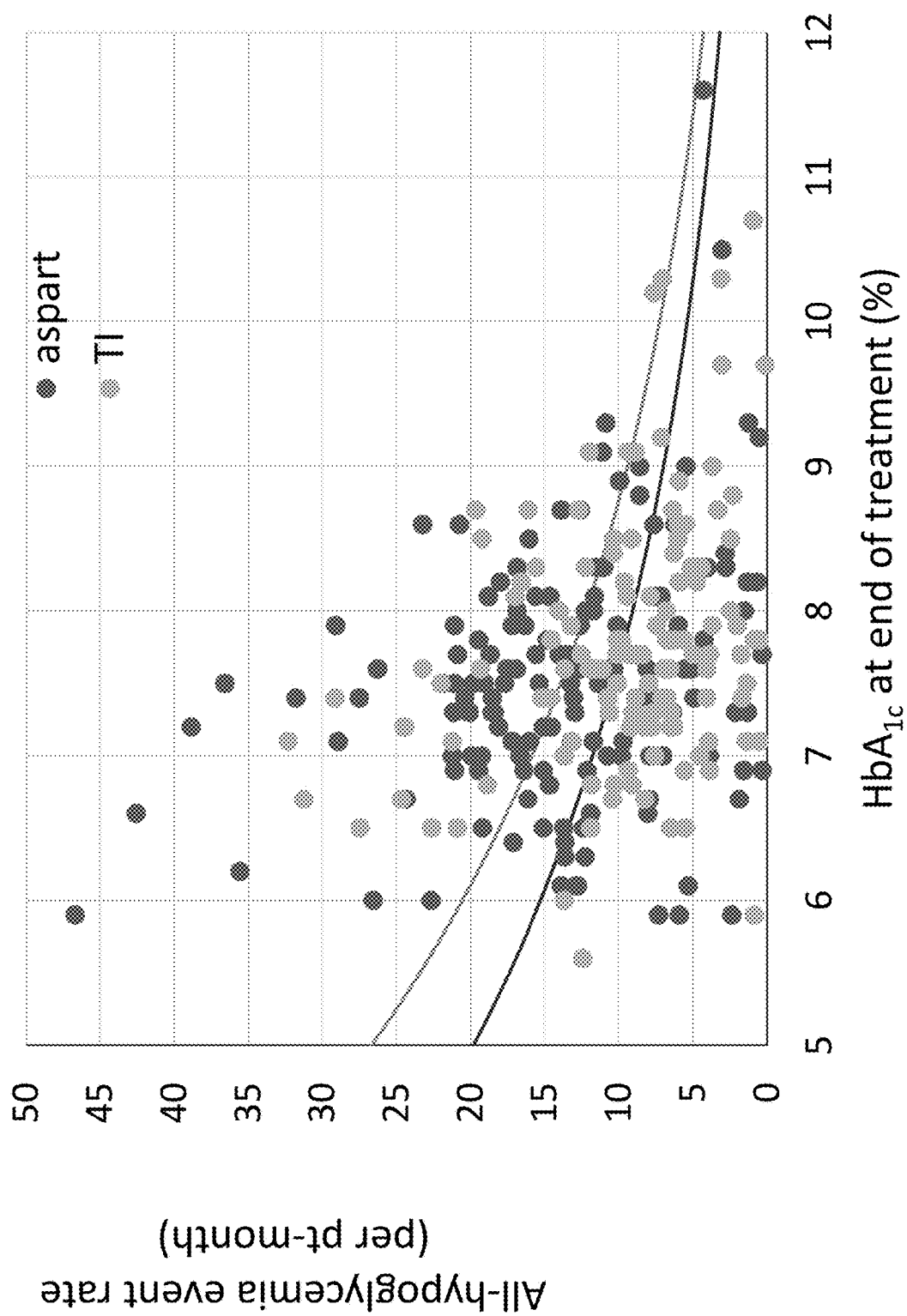
FIG. 1 depicts a graphic representation of data obtained from clinical studies of patients treated with the instant ultra-rapid acting insulin (TI, grey/open circles) compared to a rapid acting insulin analog, insulin aspart (solid circles), demonstrating the hypoglycemic event rates as a function of $HbA_{1c}$.

Prior to setting forth the detailed disclosure, it may be helpful to provide an understanding of certain terms that will be used hereinafter:

Dry powder: As used herein "dry powder" refers to a fine particulate composition that is not suspended or dissolved in a propellant, carrier, or other liquid. It is not meant to imply a complete absence of all water molecules.

First-Phase: As used herein, "first-phase" refers to the spike in insulin levels as induced by a bolus intravenous injection of glucose. A first-phase insulin release generates a spike in blood insulin concentration that is a rapid peak which then decays relatively quickly.

Early phase: As used herein "early phase" refers to the rise in blood insulin concentration induced in response to a meal which peaks within 20-30 minutes. The distinction between early phase and first phase is not always carefully adhered to in the general literature.

Excursion: As used herein, "excursion" refers to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating.

Glucose elimination rate: As used herein, "glucose elimination rate" (GER) is the rate at which glucose disappears from the blood. Using a glucose clamp it can be determined as the glucose infusion rate required to maintain stable blood glucose, often around 120 mg/dL during a glucose clamp experimental procedure. This glucose elimination rate is equal to the glucose infusion rate, abbreviated as GIR.

Honeymoon phase: As used herein, the "honeymoon phase" of type 1 diabetes refers to the early stages of the disease characterized by loss of early phase insulin release and the remaining □-cell function produces some insulin, which is released with second-phase kinetics.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 70 mg/dL, or less than 63 mg/dL (3.5 mM). Clinically relevant hypoglycemia is defined as blood glucose concentration below 63 mg/dL or causing patient symptoms such as cognitive impairment, behavioral changes, pallor, diaphoresis hypotonia, flush and weakness that are recognized symptoms of hypoglycemia and that disappear with appropriate caloric intake. Severe hypoglycemia is defined as a hypoglycemic episode that required glucagon injections, glucose infusions, or help by another party.

In proximity: As used herein, "in proximity," as used in relation to a meal, refers to a period near in time to the beginning of a meal.

Insulin composition: As used herein, "insulin composition" refers to any form of insulin suitable for administration to a mammal and includes insulin isolated from mammals, recombinant insulin, insulin associated or derivatized with other molecules, and insulin molecules with altered sequences, so long as they retain clinically relevant blood glucose lowering activity. Also included are compositions of insulin suitable for administration by any route including pulmonary, subcutaneous, nasal, oral, buccal and sublingual. Insulin compositions can be formulated as dry powders, aqueous solutions or suspensions, or non-aqueous solutions or suspensions (as is typical for metered dose inhalers) for inhalation; aqueous solutions or suspensions for subcutaneous, sublingual, buccal, nasal or oral administration; and solid dosage forms for oral and sublingual administration.

Insulin-related disorder: As used herein, "insulin-related disorders" refers to disorders involving production, regulation, metabolism, and action of insulin in a mammal. Insulin-related disorders include, but are not limited to, pre-diabetes, type 1 diabetes mellitus, type 2 diabetes mellitus, hypoglycemia, hyperglycemia, insulin resistance, secretory dysfunction, loss of pancreatic □-cell function, and loss of pancreatic β-cells.

Non-insulin dependent patients having insulin-related disorders: As used herein "non-insulin dependent patients having insulin-related disorders" refers to patients with disorders for which therapy with exogenously-provided insulin is not the current standard treatment upon diagnosis. Non-insulin dependent patients having insulin-related disorders which are not treated with exogenously-administered insulin include early type 2 diabetes, type 1 diabetes in the honeymoon phase, pre-diabetes and insulin-producing cell transplant recipients.

Insulin resistance: As used herein, the term "insulin resistance" refers to the inability of a patient's cells to respond to insulin appropriately or efficiently. The pancreas responds to this problem at the cellular level by producing more insulin. Eventually, the pancreas cannot keep up with the body's need for insulin and excess glucose builds up in the bloodstream. Patients with insulin resistance often have high levels of blood glucose and high levels of insulin circulating in their blood at the same time.

Insulin resistance spectrum: As used herein "insulin resistance spectrum" refers to the range over which the degree to which a patient is resistant to insulin can vary. It is well understood that from person to person, and from one point in the progression of type 2 diabetes to another the degree of insulin resistance can differ. Although there are no generally accepted units of insulin resistance it is well within the ability of one of ordinary skill in the art to recognize a lower degree of insulin resistance as opposed to a higher degree of insulin resistance. Ideally insulin resistance can be measured with euglycemic clamp procedures, but these are not practical for routine use. Simpler assessments include HOMA (see Matthew D R, Hosker J P, Rudenski A S, et al., Homeostasis model assessment: insulin resistance and β-cell function from fasting plasma glucose and insulin concentrations in man, Diabetologia 1985; 28:412-419) and the related QUICKI (Katz A, Nambi S S, Mather K, Baron A D, Follmann D A, Sullivan G, Quon M J. Quantitative insulin sensitivity check index: a simple, accurate method for assessing insulin sensitivity in humans. J Clin Endocrinol Metab. 2000 July; 85(7):2402-10). Fasting serum insulin levels themselves can also be used as an indicator of the degree of insulin resistance with concentrations of 50-100 pmol/L indicating resistance at the lower end of the spectrum and concentrations of 300 pmol/L indicating resistance at the higher end of the spectrum. Finally, for patients already on an insulin treatment, the total daily dose is commonly taken as an indicator of whether the subject has a high or low degree of insulin resistance.

Intermediate acting insulin: As used herein, "intermediate acting insulin" or lente insulin, refers to an insulin with an onset of action usually about two to four hours after injection and peaks four to 12 hours after injection, and it keeps working for 10 to 18 hours. Typical intermediate acting insulins are obtained by mixing regular insulin with a substance that makes the body absorb the insulin more slowly. A non-limiting example is NPH insulin. Intermediate acting insulin can provide many of the benefits of long acting insulin.

Long acting insulin: As used herein, the term "long acting insulin" refers to an insulin formulation that starts working within about 1-6 hours and provides a continuous level of insulin activity for up to 24 hours or more. Long-acting insulin operates at maximum strength after about 8-12 hours, sometimes longer. Long-acting insulin is usually administered in the morning or before bed. Non-limiting examples of long acting insulin include, but are not limited to, insulin glargine or insulin detemir, which are insulin analogs, and ultralente insulin which is regular human insulin formulated to slow absorption. Long acting insulin is best suited to provide for basal, as opposed to prandial, insulin requirements.

Meal: As used herein, "meal", "meals", and/or "mealtime", etc. include traditional meals and meal times; however, these also include the ingestion of any sustenance regardless of size and/or timing. As used herein "established meal" refers specifically to the daily periods of primary food consumption such as the usual or traditional three daily meals. Some diabetics are encouraged to eat four somewhat smaller daily meals to reduce peak blood glucose levels; such meals are also included within the meaning of the term established meal.

Microparticles: As used herein, the term "microparticles" includes microcapsules having an outer shell composed of either a diketopiperazine alone or a combination of a diketopiperazine and one or more drugs. It also includes microspheres containing drug dispersed throughout the sphere; particles of irregular shape; and particles in which the drug is coated on the surface(s) of the particle or fills voids therein.

Prandial: As used herein, "prandial" relates something to a meal or a snack. Depending on context in can refer to a period of time less than an hour after beginning a meal, or for as long as consumption of food continues.

Periprandial: As used herein, "periprandial" refers to a period of time starting shortly before and ending shortly after the ingestion of a meal or snack.

Postprandial: As used herein, "postprandial" refers to a period of time, generally an hour or more, after beginning a meal and after ingestion of a meal is completed. As used herein, late postprandial refers to a period of time beyond 2 hours after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Pre-Diabetic: As used herein, the term "pre-diabetic" refers to a patient with impaired fasting glucose impaired glucose tolerance, that is with a fasting blood glucose level between 100 mg/dL (5.5 mmol/L) and 126 mg/dL (7.0 mmol/L), or a 2 hour post-prandial blood glucose level between 140 mg/dL (7.8 mmol/L) and 200 mg/dL (11.1 mmol/L).

Rapid acting insulin: As used herein, the term "rapid acting insulin" refers to an insulin formulation that reaches peak blood concentration in approximately 45-90 minutes and peak activity approximately one to 3 hours after administration. Rapid acting insulin can remain active for about four to six hours. A non-limiting example of a rapid acting insulin is the insulin analog insulin lispro (HUMALOG®). The withdrawn product EXUBERA® and the experimental formulation VIAJECT® (Biodel Inc.), both based on regular human insulin, have kinetic profiles falling within this definition.

Second-Phase: As used herein, "second-phase" refers to the non-spiking release of insulin in response to elevated blood glucose levels. This is distinct from "second-phase kinetics" which refers to the slow decay of modestly elevated blood insulin levels back to baseline.

Short acting insulin: As used herein the term "short acting insulin" includes regular insulin and the rapid acting preparations, typically used around mealtimes.

Snack: As used herein "snack" refers specifically to food consumed between established meals.

Suppressor of hepatic glucose output: As used herein, the phrase "suppressor of hepatic glucose output" refers to drugs which suppress hepatic glucose production (hepatic gluconeogenesis, mobilization from glycogen stores). A non-limiting example of a suppressor of hepatic glucose output is metformin.

As used herein, "diketopiperazine" or "DKP" includes diketopiperazines and salts, derivatives, analogs and modifications thereof falling within the scope of the general Formula 1, wherein the ring atoms E1 and E2 at positions 1 and 4 are either 0 or N and at least one of the side-chains R1 and R2 located at positions 3 and 6 respectively contains a carboxylic acid (carboxylate) group. Compounds according to Formula 1 include, without limitation, diketopiperazines, diketomorpholines and diketodioxanes and their substitution analogs.

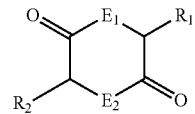

Formula 1

Diketopiperazine microparticles, in addition to making aerodynamically suitable microparticles enabling delivery to the deep lung, also rapidly dissolve and release any drug cargo further speeding absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules.

In another embodiment of the present invention, the DKP is a derivative of 3,6-di(4-aminobutyl)-2,5-diketopiperazine, which can be formed by (thermal) condensation of the amino acid lysine. Exemplary derivatives include 3,6-di (succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5,352,461, 5,503,852, 6,071,497, and 6,331,318, each of which is incorporated herein by reference for all that it teaches regarding diketopiperazines and diketopiperazine-mediated drug delivery). The use of DKP salts is described in co-pending U.S. patent application Ser. No.

11/210,710 filed Aug. 23, 2005, which is hereby incorporated by reference for all it teaches regarding diketopiperazine salts. Pulmonary drug delivery using DKP microparticles is disclosed.

As used herein the term "a unit dose inhaler" refers to an inhaler that is adapted to receive a single cartridge or container comprising a dry powder formulation and delivers a single dose of a dry powder formulation by inhalation from a single container to a user. It should be understood that in some instances multiple unit doses will be required to provide a user with a specified dosage.

As used herein a "cartridge" is an enclosure configured to hold or contain a dry powder formulation, a powder containing enclosure, which has a cup or container and a lid. The cartridge is made of rigid materials, and the cup or container is moveable relative to the lid in a translational motion or vice versa.

As used herein a "powder mass" is referred to an agglomeration of powder particles or agglomerate having irregular geometries such as width, diameter, and length.

As used herein a "unit dose" refers to a pre-metered dry powder formulation for inhalation. Alternatively, a unit dose can be a single container having multiple doses of formulation that can be delivered by inhalation as metered amounts. A unit dose cartridge/container contains a single dose. Alternatively it can comprise multiple individually accessible compartments, each containing a unit dose.

As used herein, the term "about" is used to indicate that a value includes the standard deviation of error for the device or method being employed to determine the value.

As used herein, the term "microparticle" refers to a particle with a diameter of about 0.5 to about 1000 μm, irrespective of the precise exterior or interior structure. Microparticles having a diameter of between about 0.5 and about 10 microns can reach the lungs, successfully passing most of the natural barriers. A diameter of less than about 10 microns is required to navigate the turn of the throat and a diameter of about 0.5 μm or greater is required to avoid being exhaled. To reach the deep lung (or alveolar region) where most efficient absorption is believed to occur, it is preferred to maximize the proportion of particles contained in the "respirable fraction" (RF), generally accepted to be those particles with an aerodynamic diameter of about 0.5 to about 6 μm, though some references use somewhat different ranges, as measured using standard techniques, for example, with an Anderson Cascade Impactor. Other impactors can be used to measure aerodynamic particle size such as the NEXT GENERATION IMPACTOR™ (NGI™, MSP Corporation), for which the respirable fraction is defined by similar aerodynamic size, for example <6.4 μm. In some embodiments, a laser diffraction apparatus is used to determine particle size, for example, the laser diffraction apparatus disclosed in U.S. Pat. No. 8,508,732, which disclosure is incorporated herein in its entirety for its relevant teachings related to laser diffraction, wherein the volumetric median geometric diameter (VMGD) of the particles is measured to assess performance of the inhalation system. For example, in various embodiments cartridge emptying of ≥80%, 85%, or 90% and a VMGD of the emitted particles of <12.5 μm, <7.0 μm, or <4.8 μm can indicate progressively better aerodynamic performance.

Respirable fraction on fill (RF/fill) represents the percentage (%) of powder in a dose that is emitted from an inhaler upon discharge of the powder content filled for use as the dose, and that is suitable for respiration, i.e., the percent of particles from the filled dose that are emitted with sizes suitable for pulmonary delivery, which is a measure of microparticle aerodynamic performance. As described herein, a RF/fill value of 40% or greater than 40% reflects acceptable aerodynamic performance characteristics. In certain embodiments disclosed herein, the respirable fraction on fill can be greater than 50%. In an exemplary embodiment, a respirable fraction on fill can be up to about 80%, wherein about 80% of the fill is emitted with particle sizes <5.8 μm as measured using standard techniques.

As used herein, "amorphous powder" refers to dry powders lacking a definite repeating form, shape, or structure, including all non-crystalline powders.

DETAILED DESCRIPTION

In embodiments disclosed herein, composition, methods and dry powder inhalers for treating hyperglycemia in patients with diabetes are disclosed. The dry powders inhalers comprise a cartridge for delivering dry powders including pharmaceutical medicaments to a subject by oral inhalation are described. In one embodiment, the dry powder inhaler is a breath-powered, dry powder inhaler, and the cartridge is designed to contain an inhalable dry powder, including but not limited to pharmaceutical formulations comprising an active ingredient, including a pharmaceutically active substance, and optionally, a pharmaceutically acceptable carrier.

The dry powder inhalers are provided in various embodiments of shapes and sizes, and can be reusable, easy to use, inexpensive to manufacture and/or produced in high volumes in simple steps using plastics or other acceptable materials. Various embodiments of the dry powder inhalers are provided herein and in general, the inhalation systems comprise inhalers, powder-filled cartridges, and empty cartridges. The present inhalation systems can be designed to be used with any type of dry powder. In one embodiment, the dry powder is a relatively cohesive powder which requires optimal deagglomeration conditions. In one embodiment, the inhalation system provides a re-useable, miniature breath-powered inhaler in combination with single-use cartridges containing pre-metered doses of a dry powder formulation.

In some embodiments herewith, the drug content of the inhaler can be delivered on crystalline powders using FDKP as the carrier or excipient, and which are lyophilized or sprayed dried powders at contents to about 10%, or about 20%, or about 30% or higher of the total weight of the formulation. In these embodiments, the carrier particles can be pre-formed, crystalline particles, wherein the particles are formed in a bulk powder and the insulin or active agent is added to the particles in a suspension so that the active agent can adhere to the surface of the particles.

In embodiments using microcrystalline particles formed from FDKP, or FDKP disodium salt, and wherein the particles do not self-assemble in suspension when formed and comprise submicron size particles, drug content can typically be greater than 0.01% (w/w). In one embodiment, the drug content to be delivered with the microcrystalline particles is from about 0.01% (w/w) to about 75% (w/w); from about 1% to about 50% (w/w), from about 10% (w/w) to about 25% (w/w), or from about 10% to about 20% (w/w), or from 5% to about 30%, or greater than 25% depending on the drug to be delivered. An example embodiment wherein the drug is a peptide such as insulin, the present microparticles typically comprise approximately 10% to 45% (w/w), or from about 10% to about 20% (w/w) insulin. In certain embodiments, the drug content of the particles can vary depending on the form and size of the drug to be delivered.

In an exemplary embodiment, the composition comprises a dry powder comprising microcrystalline particles of fumaryl diketopiperazine, wherein the insulin is adsorbed to the particles and wherein the content of the insulin in the composition comprises up to about 1-20% (w/w) and ranges from about 0.5% to about 10% (w/w), or from about 1% to about 5% (w/w) of the dry powder. In one embodiment, the composition herein can comprise other excipients suitable for inhalation such as amino acids including methionine, isoleucine and leucine. In this embodiment, the insulin composition can be used in the prevention and treatment of diabetes by self-administering an effective dose comprising about 1 mg to 15 mg of a dry powder composition comprising crystalline, microcrystalline, crystalline composite or amorphous form of fumaryl diketopiperazine and insulin in a single inhalation. In a particular embodiment, the insulin content in the formulation can be from about 1 mg to about 20 mg. In one embodiment, the dry powder content of the cartridges comprising insulin can be 4 units, 8 units, 12 units, 16 units, 20 unites, 24 units and up to 90 units.

In alternate embodiments, the pharmaceutically acceptable carrier for making dry powders can comprise any carriers or excipients useful for making dry powders and which are suitable for pulmonary delivery. Example of suitable carriers and excipients include, sugars, including saccharides and polysaccharides, such as lactose, mannose, sucrose, mannitol, trehalose; citrates, amino acids such as glycine, L-leucine, isoleucine, trileucine, tartrates, methionine, vitamin A, vitamin E, zinc citrate, trisodium citrate, zinc chloride, polyvinylpyrrolidone, polysorbate 80, phospholipids including diphosphotidylcholine and the like.

In one embodiment, a method of self-administering a dry powder formulation to one's lung(s) with a dry powder inhalation system is also provided. The method comprises: obtaining a dry powder inhaler in a closed position and having a mouthpiece; obtaining a cartridge comprising a pre-metered dose of a dry powder formulation in a containment configuration; opening the dry powder inhaler to install the cartridge; closing the inhaler to effectuate movement of the cartridge to a dose position; placing the mouthpiece in one's mouth, and inhaling once deeply to deliver the dry powder formulation.

In still yet a further embodiment, a method of treating hyperglycemia in insulin resistance diabetes patients is disclosed. The method comprises, administrating an inhalable dry powder composition or formulation comprising, for example, a diketopiperazine having the formula 2,5-diketo-3,6-di(4-X-aminobutyl)piperazine, wherein X is selected from the group consisting of succinyl, glutaryl, maleyl, and fumaryl and an insulin. In this embodiment, the dry powder composition can comprise a diketopiperazine salt. In still yet another embodiment, there is provided a dry powder composition or formulation, wherein the diketopiperazine is 2,5-diketo-3,6-di-(4-fumaryl-aminobutyl)piperazine, with or without a pharmaceutically acceptable carrier, or excipient.

In another embodiment, the method of treating diabetes comprises providing an inhalation system for delivering a dry powder formulation to a patient's lung(s), the system comprising a dry powder inhaler configured to have rigid flow conduits with a total resistance to flow in a dosing configuration ranging in value from 0.065 to about 0.200 ($\sqrt{kPa}$)/liter per minute.

In one embodiment, a dry powder inhalation kit is provided comprising a dry powder inhaler as described above, one or more medicament cartridges comprising a dry powder formulation for treating a disorder or disease such as respiratory tract and lung disease, diabetes and obesity.

Methods of treating a disease or disorder in a patient with the dry powder inhaler embodiments disclosed herewith is also provided. The method of treatment comprises providing to a patient in need of treatment a dry powder inhaler comprising a cartridge containing a dose of an inhalable formulation comprising an insulin dry powder and a pharmaceutical acceptable carrier and/or excipient; and having the patient inhale through the dry powder inhaler deeply for about 3 to 4 seconds to deliver the dose. In the method, the patient can resume normal breathing pattern thereafter.

The following examples illustrate some of the processes for making dry powders suitable for using with the inhalers described herein and data obtained from experiments using the dry powders. Insulin-FDKP was discovered to be an ultra-rapid acting insulin capable of mimicking physiologic mealtime early phase insulin release. In exploring how an insulin preparation with this unique pharmacokinetic profile might be used advantageously in the treatment of type 1 and 2 diabetes, it has up to now been evaluated in comparison to other insulin preparations (see for example, U.S. patent application Ser. No. 11/461,746; U.S. Pat. Nos. 7,943,572 and 9,006,175, each of which are hereby incorporated by reference in their entirety). Embodiments disclosed herein are concerned with how specific dosages and modes of administration for such insulin preparations can be chosen for individual patients and applied to various patient populations for advantageous effect. Certain embodiments are concerned with how such insulin preparations can be used in combination with and/or in place of oral antidiabetic medications, particularly insulin sensitizers and insulin secretagogues, to achieve similar or advantageous effect. Certain other embodiments are concerned with how such insulin preparations can be used in combination with and/or in place of exogenously provided basal insulins to achieve similar or advantageous effect. Similar disclosure is also found in U.S. Pat. Nos. 8,119,593; 8,258,095 and 10,046,031 each of which is incorporated herein by reference in its entirety.

In general, various embodiments involve the use of prandial ultra-rapid acting insulin in defined populations. These populations may be referred to as being in need of, capable of benefiting from, or desirous of receiving the benefit of one or another or more of the advantages offered by the various methods described. Such advantages can be expressed as receiving or seeking some stated clinical benefit. Such advantages can also include elimination or avoidance of various side-effects, adverse outcomes, contraindications, and the like, or reducing the risk or potential for them to occur. Similarly the methods can involve a step of selecting a patient on the basis of being part of one or another of populations. It should be understood that selecting can comprise a physician or other healthcare professional evaluating a patient in respect to the particular parameters but can also comprise a self-selection by the patient to be treated on the basis of similar data or in accepting the advice of the physician or other healthcare professional. In like manner, administering steps of these methods can comprise the physical taking of a medicament (or similarly discontinuing treatment with a medicament) by a patient but can also comprise a physician or other healthcare professional prescribing or providing other specific instruction to take (or discontinue) a medicament. Further embodiments of the invention include use of ultra-rapid acting insulin preparations, compositions, or formulations for such purposes, and in the manufacture of medicaments for such purposes.

As used herein, mimicking physiologic mealtime early phase insulin release (or similar terms) does not necessarily indicate exact replication of all features of the physiologic response. It can refer to insulin preparations and methodologies producing a spike or peak of insulin concentration in the blood that constitutes both a relatively quick rise and fall in concentration. In certain embodiments, the rise to peak concentration takes less than 30 minutes, preferably less than about 20 minutes, or about 15 minutes, and in further embodiments the rise to peak insulin concentration may take at least 5 or at least 10 minutes. For example, in a non-diabetic subject, insulin release from the pancreas during a meal can reach a peak insulin concentration in blood in about 12-14 minutes or 10-20 minutes, or longer from food intake, or first departure from baseline, and a decrease from peak insulin concentration involves a descent through half maximal concentration by 80 minutes, alternatively 50 minutes, or alternatively 35 minutes after peak and insulin concentration will be approaching baseline with 2 to 3 hours of food intake or sooner.

Exogenously administered insulin-FDKP by oral inhalation with a high resistance inhaler substantially mimics native insulin release during a meal in non-diabetic patients; wherein upon administration by inhalation to a patient with diabetes, insulin peak concentration in blood is reached within 30 minutes and often less than 20 minutes after administration and return to baseline levels in less than 2 hours after administration. This is in contrast to injectable, rapid acting insulin analog preparations and which methods of delivery produce a more gradual rise (from 30 minutes to several hours) to the maximal insulin concentration achieved and a prolonged plateau near maximal concentrations and remain in the blood at elevated levels for up to 6 hours after administration that can lead often to hypoglycemic events. The rapid acting analogs (RAA) do show a greater degree of peaking than regular human insulin, but even the fastest of the commercially available RAAs, as disclosed in their prescribing information, insulin lispro (Humalog®) reports a $T_{max}$ of 30-90 minutes. For comparison, insulin aspart (Novolog®) reports a median $T_{max}$ of 40-50 minutes in subjects with type 1 diabetes and insulin glulisine (Apidra®) reports a median $T_{max}$ of 60 and 100 minutes in subjects with type 1 and type 2 diabetes, respectively, with a range of 40-120 minutes in both populations.

In the present embodiments, mimicking physiologic mealtime, early phase insulin release can also refer to insulin preparations and methodologies in which the insulin spike or maximal insulin concentration in blood can be reliably coordinated with the start of a meal, which can achieve maximal glucose elimination rate ($GER_{max}$) within about 30-90 minutes, preferably around 45-60 minutes, after administration. Insulin preparations with such characteristics are referred to herein as ultra-rapid acting. In embodiments herewith, mimicking early phase release is generally also one that can be practiced by diabetics upon themselves without special medical training, such as training in intravenous injection. With the present dry powder inhalers less training is required from medical professionals and users, they are easy to use. In some embodiments ultra-rapid acting insulin can be administered with every meal of any type of foods regardless of size and/or timing. Nonetheless, it is preferred that inhaled insulin be administered only for a meal providing at least a threshold glycemic load (which can depend on the insulin dose) so as to avoid a risk of hypoglycemia. Various methods of assessing glycemic load are known in the art including "carb counting" (calculating/estimating the number of grams of carbohydrate in a meal), the use of bread exchanges, and consideration of the glycemic index of the foods to be consumed. Supplemental doses of inhaled insulin can be administered if blood sugar levels remain at undesirable levels postprandially.

The meaning of ultra-rapid can also be understood by further comparison to other insulin preparations. Regular human insulin preparations for subcutaneous injection are considered short acting, referring primarily to their duration of action. Typically, they will take at least 1-2 hours to reach maximal blood insulin concentration and can take 2-4 hours to reach maximal activity. Significant elevation or activity can last for as long as 10-12 hours. Other short acting insulins include the rapid acting insulin analogs such as insulin aspart, insulin glulisine, and insulin lispro. Because these insulin preparations more readily dissociate from hexamer to monomer upon injection they reach peak blood concentrations sooner (30-100 minutes) and consequently also have a faster onset of action than regular human insulin. Insulin preparations for pulmonary administration, such as the now withdrawn product Exubera® display pharmacodynamics similar to the rapid acting analogs. A comparison of the pharmacodynamic profiles of several pulmonary formulations, insulin lispro, and insulin-FDKP has been published showing that insulin-FDKP is distinctly faster in reaching maximal activity and declines toward baseline sooner (Heinemann et al. *Br. J. Diab. Dis* 4:295-301, 2004). Thus, whereas an ultra-rapid acting insulin will have expended approximately two thirds of its insulin lowering activity within 2 hours after administration these other preparations will typically have expended about a third or less of their insulin lowering activity in that same time frame. At the other end of the spectrum are the long acting insulins, such as insulin glargine or insulin detemir which ideally provide a constant level of insulin activity over long periods of time, for example up to 24 hours. These are intended to provide basal activity and are typically administered once or twice a day. As such, the rapidity of onset of action is not a critical parameter. Finally, there are insulin preparations, termed intermediate acting, with durations of action between the short and long acting products.

The potentiation of glucose elimination rate, GER contributing to the rapid attainment of $GER_{max}$ is understood to depend not only on the rapidity of the rise in insulin concentration, but also on achieving sufficient peak height. For type 1 diabetics, this is a peak insulin concentration of at least about 60 mU/L, preferably at least about 80 mU/L. For type 2 diabetics the insulin resistance that is part of the condition can necessitate higher insulin concentrations; typically at least about 100 mU/L, preferably at least about 120 mU/L, at least about 140 mU/L, or more, depending on the degree of resistance. Thus, in various embodiments herewith, the instant insulin-FDKP delivery achieves peak height of at least 60, 100, or 120 mU/L above the pre-dosing insulin concentration baseline. The peak insulin concentrations achieved with present inhaled insulin are substantially higher than those attained with typical doses of non-spiking insulin products such as standard preparations for subcutaneous administration, including those termed rapid- or fast-acting, and preparations for non-injected administration having similar kinetics that have been described.

The comparatively slow and shallow rise in insulin concentration and prolonged period of action associated with insulin preparations that do not mimic early phase release, limits their ability to control glucose excursions. The dose that can be given is generally inadequate to control the rise in blood glucose following a meal due to the need to avoid inducing hypoglycemia after the glycemic load from the meal has been abated. These issues are further discussed in U.S. Pat. No. 8,119,593, which is incorporated herein by reference in its entirety. It is emerging that acute fluctuations in blood glucose concentrations (measured, for example, as MAGE: mean amplitude of glycemic excursions) have a greater effect than chronic hyperglycemia (typically measured as Hb1Ac level) on diabetes-associated oxidative stress, and thus is an important parameter to control to avoid diabetic complications attributable to such stress (see Monnier, L., et al. JAMA 295:1681-1687, 2006; and Brownlee, M. & Hirsch, I. JAMA 295:1707-1708, which are incorporated herein by reference in their entirety). It is the applicant's further understanding that a high surge and rapid rate of change in insulin concentration suppresses glucagon production, reducing hepatic glucose release. This results in a lessened glycemic load and consequently lessened demand for insulin and reduced glucose excursion.

Ultra-rapid acting insulin is particularly well suited to the control of postprandial blood glucose (PPG). (For a review of the significance of PPG see MannKind Corporation. Postprandial hyperglycemia: Clinical significance, pathogenesis, and treatment. Valencia, Calif.: MannKind Corporation; 2009:1-20). The ultra-rapid kinetics not only enable better matching of insulin activity to the time when glucose is being absorbed from a meal, there is also similarly quicker and advantageously timed suppression of hepatic glucose output. Thus, it addresses both sources of glucose contributing to postprandial hyperglycemia. Embodiments disclosed herein seek to constrain 1 and 2 hour PPG to ≤140 mg/dl, ≤180 mg/dl, or ≤200 mg/dl. Surprisingly, it has also become apparent that control of PPG levels has long term beneficial effects on fasting blood glucose levels as well. Through consideration of these properties and the data from clinical use, it is herein disclosed how ultra-rapid acting insulins such as insulin-FDKP may be advantageously used in particular patient populations alone, or in combination with standard oral antidiabetic medications and in contrast to current treatment paradigms in type 2 diabetes therapy.

Treatment of diabetes has traditionally focused on controlling average blood glucose concentrations, as reflected by HbA1c levels. The presently disclosed methods are designed to minimize not only HbA1c levels (average blood glucose concentration) and attendant glucose toxicity; but also to control acute fluctuations in glucose concentration (glucose excursions). The reduction of glucose excursions also relieves the general inflammatory burden and oxidative damage to microvasculature resulting from oxidative stress. Thus, even for patients in whom substitution of ultra-rapid insulin for one or more oral medications may result in only similar control of HbA1c levels the treatment can confer a benefit over treatment with oral medications alone. This is a benefit that is also not attainable by addition of basal insulin to the treatment regimen. Nor can the merely rapid acting insulins be expected to deliver this benefit in full measure, especially as compared to an optimized dose of an ultra-rapid acting insulin.

This benefit is accomplished by routinely administering an insulin preparation that mimics early phase release, that is an ultra-rapid acting insulin preparation, in conjunction with at least one, preferably at least two or three meals a day, or with every established meal, or with every meal including snacks. Such treatment should be maintained, in increasing preference and for increasing effectiveness, for any number of days, weeks, months, and years, up to the remainder of the patient's life (or until such time as the underlying insulin-related disorder is cured or otherwise alleviated). By routinely, it is meant that the advocated schedule of administration is the ideal and usual usage, but real world practice deviations from this protocol, such as occasional missed meals or missed doses, do not depart from the scope of the claims. In various embodiments, ultra-rapid acting insulin is routinely administered with any meal or snack that would otherwise cause blood glucose to exceed 140 mg/dL, or alternatively 180 mg/dl; with any meal or snack constituting 1, 2, 3, or more bread exchanges; with any meal or snack containing more than about 15, 20, 30, or 45 g of carbohydrate.

Embodiments of the methods disclosed herein include a variety of dosing regimens including, but not limited to, dosing at every meal or snack, dosing at every meal or snack having a carbohydrate content of more than 15 g, dosing at every meal or snack having a carbohydrate content of more than 30 g, dosing at every meal or snack having a carbohydrate content of more than 45 g. Dosages and desired insulin composition concentrations may vary depending on the particular use envisioned. The determination of the appropriate dosage or route of administration is generally within the skill of an ordinary physician. However physicians are most commonly familiar with liquid formulations of insulin which allow for the continuous variation of dose. Insulin-FDKP is supplied as a dry powder in premeasured unit doses. Therefore specific instructions for determining the appropriate dosages of insulin-FDKP for an individual are disclosed herein. Furthermore, the length of treatment may vary on the particular use and determination of the length of treatment is within the skill of an ordinary physician.

The rapid absorption and lack of a substantial tail in the activity profile of ultra-rapid acting insulin preparations, such as insulin-FDKP, also mean that they pose a reduced potential for inducing hypoglycemia as compared to other insulins. Snacking to counteract late postprandial hypoglycemia is understood to contribute to the weight gain associated with standard insulin therapies. In contrast, use of insulin-FDKP has been associated with a lack of weight gain; indeed weight loss has been observed in patients treated.

Intravenous injection of insulin can effectively replicate the first phase response and approximate the early phase response, but is not a practical therapy for a lifelong condition requiring multiple daily administrations. For these reasons, insulin for intravenous injection is not contemplated by the term ultra-rapid acting insulin preparations as used herein. Traditional subcutaneous injections are absorbed into the bloodstream slowly by comparison, even using fast acting injectable formulations, which still take up to an hour to reach maximal concentration in the blood and have a plateau lasting several hours. Many pulmonary formulations that have been assessed are equivalent to subcutaneous insulin in effectiveness and similarly fail to achieve the ultra-rapid kinetics needed to mimic early phase release, as defined above. The present inhaled formulation leads to fast absorption and rapid glucose elimination, which occurs faster than with oral tablet therapy or subcutaneous injectables.

In particular embodiments, a therapeutic method is provided that achieves the desirable early phase-like kinetics, wherein a patient is administered by pulmonary administration of a dry powder insulin formulation containing insulin complexed to diketopiperazine microparticles. This formulation is rapidly absorbed reaching peak serum levels within about 10 to 15 minutes. The insulin-FDKP formulation is fast enough to mimic the kinetics of the physiologic meal-related early phase insulin response. The short, sharp rise to peak serum insulin concentration is critical to the rapid suppression of endogenous glucose production and has the additional effect of compressing the bulk of insulin action to the peri-prandial time interval, in contrast with slower acting formulations. This reduces the magnitude and duration of any meal-related excursions from normal glucose levels and associated glucose toxicity, as well as reducing the risk of post-prandial hypoglycemia. Such improved control of blood glucose levels is obtainable with this dry powder insulin and is more fully described in U.S. Pat. No. 8,119, 593, which is incorporated herein by reference in its entirety. As disclosed in U.S. Pat. No. 8,623,817 and noted above, prior high insulin levels potentiate glucose elimination rate, meaning glucose can be eliminated more quickly if there is a prior high insulin concentration spike or sharp peak increase.

Whether insulin-FDKP or another insulin mimicking early phase release is administered alone or in conjunction with another agent, such as basal insulin, a suppressor of hepatic glucose release such as metformin, or an insulin sensitizing medication for example a thiazolidinedione (TZD), the ultra-rapid acting insulin is administered in association with established meals, at least once and preferably two to four times daily, or more times up to with every meal, depending upon need. In order to achieve the maximum benefit of the treatment, it should be taken over an extended period of time, preferably at least 12 weeks, more preferably at least 24 weeks still more preferably from about 6 months to about two years, and most preferably for the remaining life of the patient or until the underlying diabetes is cured.

Current treatment of diabetes generally aims to reduce HbA1c levels to 7% or below. HbA1c levels above 8% indicate that patient's current therapy should be re-evaluated. It may be desirable to achieve normal HbA1c levels, but with the currently marketed insulin products this could only be accomplished at an unacceptable risk of severe hypoglycemia. Thus patients with HbA1c levels below 8% would not usually be considered candidates for more intensive treatment, that is, for treatment with insulin especially the current prandial insulins. Even those with HbA1c above 8% but not yet receiving basal or mixed insulin would not be considered to be candidates for treatment with a prandial insulin regimen. In embodiments disclosed herein, the instant insulin-FDKP formulation reduces the risk of hypoglycemia is over standard injectable therapies, in part due to the lack of a tail, or rapid decrease in insulin concentration in blood (1-2 hours) after administration. The present ultra-rapid acting insulin also can reduce HbA1c marker to less than 7% (see FIGS. 1 and 2). Additionally, benefit can be expected from lowering blood glucose even at the high end of the normal range. For example, one study showed that the risk of cardiovascular disease events was 5-8 times higher for individuals with HbA1c>7% as compared to those with HbA1c<5%. Another study showed a progressive increase in risk of kidney disease as HbA1c went from <6% to >8%. Accordingly, in some embodiments, patients with HbA1c levels ≤6.5% or ≤6% are selected for treatment. While the methods are generally discussed in reference to human patients adaptation to non-human mammals is not beyond the scope of the disclosure or the abilities of one of skill in the related arts.

Determination of Individual Dosage

Insulin-FDKP is a dry powder formulation for inhalation that can be provided in cartridges containing a premeasured amount of powder which are inserted into an inhaler. The insulin is administered by orally inhaling through the inhaler to deliver the powder into the lungs. Cartridges containing different doses can be provided and an individual dosage can be obtained either by using a single cartridge containing the desired dosage or by using multiple cartridges (one at a time) depending on the patient's needs.

The patient can be a diabetic with inadequately controlled hyperglycemia, for example with HbA1c greater than 7%, or one with adequately controlled blood glucose levels but desiring to take advantage of other advantages obtainable with ultra-rapid acting insulin (for example, weight loss or avoidance of weight gain, reduced risk of hypoglycemia, reduced glucose excursions, etc.) and ease of use of an inhaler.

Determination of individual dosage starts with identification of the daily meal (that is breakfast, lunch, dinner, regularly occurring snack, etc.) resulting in the highest 2-hour post-prandial blood glucose levels using 7 point serum measured blood glucose, SMBG. The patient then increases/titrates up the dosage for that meal if glucose remain high. Once an appropriate insulin dosage is established for that meal, which means that the dosage is appropriate to maintain the blood glucose levels in normal range, the dosage for the daily meal leading to the next highest blood glucose level is increased/titrated, and the process is repeated until dosages for all daily meals have been determined. In one embodiment, an initial dosage is taken with a meal with unknown carbohydrate content and supplemented with a subsequent dose at 1 to 2 hours after the meal if blood glucose levels greater than desired, for example, greater than 140 to 200 mg/dL. In an alternative embodiment, the titration for all daily meals is carried out concurrently rather than sequentially if blood glucose is measured with a continuous glucose monitoring (CGM) system. Meals for which dose titration is being carried out are preferably "usual" for the patient in terms of size and food component content with little variation in these parameters.

Titration begins by taking one low-dose cartridge, for example, a 4 units of insulin-FDKP is taken with the meal(s) in question. Low dose insulin-FDKP cartridges can provide an emitted dose of, for example, 4, 6 or 12 U, 16 U, 20 U, 30 U, etc. of insulin. Most commonly the titration is carried out with 4, 8, or 12 U cartridges, but patients with smaller body masses, with lesser degrees of hyperglycemia to control, and/or lower degrees of insulin resistance may prefer to start the titration at a lower dose and/or proceed through the titration in smaller increments. For clarity, the titration is described below with respect to the 12 U dose but it should be understood that the titration could similarly be based on a 4 U, 6 U or other low-dose cartridge. Similarly even if titrating based on a cartridge that is not the lowest dose available one can use a smaller dose low-dose cartridge to provide the last increment (or decrease) in dosage as an alternative to the procedure described below.

A patient can use the initial dosage for a week. In each subsequent week the dosage for the meal is increased by the dose of the low-dose cartridge (i.e., 4-12 U) until either 1) the 2-hour post-prandial median glucose level is between 70 and 110 mg/dl, or 2) the dosage, based on emitted dose, is 72 U, or 3) an episode of hypoglycemia occurs. For episodes of mild to moderate hypoglycemia with confirmed SMBG of <70 mg/dl decrease dosage by one low dose (i.e., 12 U) cartridge and hold at that dose for one week then resume the titration. For an episode of severe hypoglycemia with confirmed SMBG <36 mg/dl decrease dosage by one low dose (i.e., 12 U) cartridge, hold at this new dose, and begin titration for next meal. In an alternative embodiment a pre-meal blood glucose between 70 and 110 mg/dl can also be used as a titration endpoint. In some embodiments the second criteria above for terminating dose escalation specifies a higher terminal dose or the criteria is not used at all.

In an alternative embodiment, the initial dosage can be estimated based on relative bioavailability from the dosage of a subcutaneously administered insulin. This becomes important in adapting the titration scheme to other formulations and inhaler systems than that used in the examples below. A more universal scale is obtained by identifying dosage according to the insulin exposure (that is the AUC of blood insulin concentration over time). As the titration is described above 12U emitted corresponds to 3-4 subcutaneous equivalent units (subQ eq) of a rapid acting insulin analog, for example, insulin aspart. Thus in various embodiments, the low dose can be, for example, about 1, 1.5, 2, 3, 4, or 5 subQ eq units which would be given by a subcutaneous injection of a rapid acting insulin analog. The limit for dose escalation can be about 18, 24, 32 or more subQ eq units.

The expression of dose in subQ eq units also facilitates migration to use of an ultra-rapid acting insulin if the patient is already on an insulin regimen. If the patient is already on a prandial insulin regimen they should start with the same subQ eq dose as they are currently using which is then titrated up or down from there basically as described above. If the patient is on a regimen with longer acting insulin alone or a mixture of short and longer acting insulins then 50% of the total daily dose should be divided by the number of daily meals and that amount of ultra-rapid acting insulin in sub/Q eq units should be used as the initial dose in the titration. In the case in which the ultra-rapid acting insulin is provided in form that does not allow an exact match to the current dosage, one can round down or round to the nearest (that is up or down) dose of the ultra-rapid acting insulin to use as the initial dose (see FIGS. 3A-3F below). In one embodiment this choice is left to the practitioner, but particular embodiments specify one or the other choice.

Accordingly, provided herein is a method of determining an individual's dosage of insulin-FDKP for a daily meal comprising the step of administering an initial dosage equivalent to one low-dose cartridge with the meal each day for a week. In each subsequent week the dosage is increased by the amount of one low-dose cartridge until a titration endpoint, or appropriate dose is reached that brings glucose levels to normal range, or wherein the titration is selected for the group of 1) achieving a 2-hour post-prandial median glucose is between 70 (or alternatively 80) and 110 mg/dl, 2) the dosage based on emitted dose is 72 U, 3) an episode of severe hypoglycemia with a confirmed SMBG <36 mg/dl occurs and the dosage is decreased by the equivalent of one low-dose cartridge, and 4) an episode of mild to moderate hypoglycemia with a confirmed SMBG of <70 (or alternatively 80) mg/dl occurs, the dosage is decreased by the equivalent of one low-dose cartridge for one week and then the titration is resumed until it reaches one of the other endpoints or the dosage is set at the level below that which produces the mild to moderate hypoglycemia or no hypoglycemia occurs.

Embodiments disclosed herein comprise a method in which the dosage for each daily meal is determined as described above for each of the daily meals in succession. This embodiment comprises determining which daily meal results in the highest 2-hour postprandial blood glucose level and titrating that meal first. In some embodiments, this determination utilizes a 7 point SMBG. The daily meal resulting in the next highest 2-hour postprandial blood glucose level is then titrated in turn. The initial dosage is administered with each meal not being titrated for with a dosage has not been determined. In alternative embodiments, dosages for all daily meals are titrated concurrently.

In one embodiment, the low-dose cartridge provides an emitted dose of 3-4 subQ eq units of insulin. In another embodiment the low-dose cartridge provides an emitted dose of 1.5-2 subQ eq units of insulin. In some embodiments the group of titration endpoints further comprises a premeal blood glucose level between 70 and 110 mg/dl.

In various alternative embodiments, the titration is based on at least three consecutive daily measurements as opposed to being carried out daily over a week as described above, or in a further alternative 3-6 daily measurements over the course of a week. In other alternative embodiments the titration is based on preprandial/pre-bedtime SMBG instead of 2 hour postprandial SMBG. That is the pre-lunch measurement is used to determine the breakfast dose, the pre-dinner measurement is used to determine the lunch dose, and the pre-bedtime measurement is used to determine the dinner dose.

Use of a Standard Dose

Traditional prandial insulin treatment has involved careful adjustment of insulin dosage to the expected glycemic load of the individual meal based on its size and content. The need for this can be avoided, or at least reduced through the use of an ultra-rapid acting insulin formulation. Traditional prandial insulin formulations, whether administered by subcutaneous injection/infusion or by inhalation, exert their effect on blood glucose level largely by elevating the glucose elimination rate over a relatively extended period of time. The total glucose elimination brought about is generally proportional to the dose administered. In contrast ultra-rapid acting insulin formulations exert their effect over a relatively constrained period of time and a greater proportion of their effect on blood glucose level is the result of rapidly reducing hepatic glucose release to basal levels. The rapid rise of blood insulin level obtained with ultra-rapid insulins potentiates a rapid rise in glucose elimination activity and also provide a signal to the liver to reduce glucose release. However, the high concentrations of insulin achieved to bring about these effects exceed the range in which glucose elimination rate (GER) is proportional to insulin concentration. Thus, while further increasing insulin dosage does lengthen the period of time over which GER is elevated, this is brought about by increasing the period of time in which the insulin concentration exceeds the range in which GER is proportional to insulin concentration. Therefore, total glucose elimination with ultra-rapid acting insulins is much less sensitive to dose. Moreover, insulin concentrations return to baseline levels sooner after administration so the effect is also constrained in time and homeostatic mechanisms reassert themselves much sooner than with the relatively longer acting traditional short-acting formulations, thereby reducing the potential for late postprandial hypoglycemia due to the activity of the exogenous insulin.

As a result, it can be feasible to set a standard dosage for each of the daily meals and use that dose without regard for variation in caloric content or glycemic load from meal to meal. The blood glucose lowering effect is related in part to reduction of hepatic glucose release, and effective reduction is achieved without careful matching of dosage to glucose or caloric intake even if a larger meal than usual is consumed. Since the present ultra-rapid acting insulin is effective with any food intake, the elevation of GER is comparatively short-lived and generally well-matched in time to the period during which a meal will increase blood glucose levels. Therefore, there is a low risk of hypoglycemia even if a smaller meal is consumed. In a particular embodiment, the caloric content and/or glycemic load of the meal is maintained within a range of from 25, 50, or 75% to 125, 150, 200 or 250%, of that of the usual meal (used in determining the standard dose). Since insulin resistance, and therefore responsiveness to insulin, does vary with circadian cycle it will generally be preferred to set a standard dose for each daily meal, though as a practical matter the standard dosage determined may be the same for different daily meals. This method can be particularly well-suited to diabetics with significant residual ability to produce insulin and regulate blood glucose levels, such as type 2 diabetics earlier in the progression of the disease.

Accordingly, provided herein are methods for treating diabetes with standardized doses that are not adjusted based on individual meal content. The method comprises prandial administration of a predetermined standard dosage of an ultra-rapid acting insulin formulation without adjustment of the dosage based on meal content. In various embodiments any or all daily meals are treated according to this method; for example, breakfast, or breakfast and lunch, or breakfast and dinner, or breakfast, lunch, and dinner, etc. In some embodiments, a single predetermined dosage is used for all meals. Preferred embodiments utilize predetermined dosages for each daily meal; that is for example, for breakfast, for lunch, for dinner, and snacks. In some embodiments meal content is assessed as caloric content. In other embodiments, meal content is assessed as glycemic load. In preferred embodiments meal content is maintained within a range of from 25, 50, or 75% to 125, 150, 200 or 250% of a usual meal used in determining the predetermined insulin dosage.

Use of Split, Supplemental, and Delayed Dosages

With traditional prandial insulin regimens, an insulin dosage is selected based on an expectation of how much food will be consumed, and then an attempt is made to conform consumption to the advance expectation. If more food is consumed, or its proportion of carbohydrate, fiber, and fat differs from usual or anticipated, it is not possible to improve glycemic control by administering a secondary dose subsequent to the meal when these factors are known with greater certainty, because of the delay between administration and onset of action with traditional formulations. In many instances wherein an initial dose is not sufficient to lower blood glucose levels timely as expected, the method further comprises administering a supplemental dose of an insulin. Administering a supplemental dose of a rapid acting insulin analog can lead frequently to moderate to severe hypoglycemia. In contrast ultra-rapid acting insulin formulations take effect so quickly that it can be advantageous to adjust the dosage of insulin to the meal by administering a secondary dose subsequent to the meal without less risk of developing hypoglycemia. See FIGS. 1, 2, 3A-3F and 4A-D wherein type 1 diabetics were treated with insulin aspart and the claimed inhaled formulation, showing a reduction in hypoglycemia events in patients treated with insulin-FDKP, TI when compared to those treated with insulin aspart. Use of split dosages can be particularly well-suited to diabetics other than type 2 diabetics with good endogenous insulin production and only moderate insulin resistance. It is also beneficial to type 1 diabetics (past the "honeymoon" stage of the disease) and type 2 diabetics later in the progression of the disease.

In one application of this mode of administration, split dosage is applied to meals in which delayed absorption is expected. The delay can be due to disease state—long-term diabetes is associated with delayed nutrient absorption; or can be due to meal content—higher fat and fiber content tend to delay food absorption. Use of split dosages can also be advantageously used in conjunction with multi-course or other prolonged meals such as at holiday celebrations and banquets. Even if the individual limits total consumption in accordance with their usual meals the fact that consumption extends over a longer than usual period of time will also lead to a prolongation of nutrient absorption. Split doses provide a way to address this prolonged profile of nutrient absorption. As compared to the dosage of insulin that would be used with the meal as a single dose of one-half to three-quarters or for example, two thirds of the dose is administered at the beginning of the meal and the remainder of the dosage is administered 30 to 120 minutes later.

Accordingly, additional embodiments provide a method of treating diabetes comprising selecting a patient expected to have delayed nutrient absorption, administering an initial dose of ½ to ¾ of a predetermined dosage of an ultra-rapid acting insulin formulation at the beginning of a meal, and administering the remainder of the predetermined dosage 30-120 minutes later. In one embodiment the initial dose is ⅔ of the predetermined dosage. In some embodiments, delayed adsorption is related to a state of the disease (diabetes). In other embodiments, delayed adsorption is related to meal content. In further aspects of these embodiments meal content comprises high fiber content. In other aspects of these embodiments, meal content comprises high fat content. In a further aspect, the high fat content constitutes ≥25% of the meal content. In a further aspect, the high fat content constitutes ≥35% of the meal content. In one embodiment, the ultra-rapid acting insulin formulation is insulin-FDKP, which is administered by inhalation into the lungs.

In another application of this mode of administration, split dosage is used to adjust the insulin dosage to the actual glycemic load. An initial dose is administered at the beginning of the meal, blood glucose level is determined 60 to 120 minutes later, and a secondary or supplemental dose is administered if blood glucose exceeds 140 mg/dl. In some embodiments the secondary dosage is equal to 50-100% of the initial dosage. In some embodiments blood glucose is determined by continuous glucose monitoring.

Accordingly, additional embodiments provide a method of treating diabetes comprising administering an initial dose of an ultra-rapid acting insulin formulation at the beginning of a meal, determining a blood glucose level 60-120 minutes after beginning the meal, and if the blood glucose level exceeds 140 (or alternatively 150) mg/dl administering a second dose of the ultra-rapid acting insulin formulation wherein the dosage of the second dose is 25% or 50% to 100% of the dosage of the initial dose.

In a variation on this mode of administration, no insulin dose is administered at the initiation of the meal. Instead, insulin administration is delayed, for example, for 10, 15, 20, or 30 minutes after beginning the meal. This variation is particularly suitable when delayed nutrient absorption is expected in the patient.

Accordingly, embodiments disclosed herein provide a method of treating diabetes comprising, administering a dose of an ultra-rapid acting insulin formulation subsequent to the beginning of a meal to a patient who experiences delayed nutrient absorption. In one embodiment, the method of treatment to a patient with diabetes and with delayed nutrient absorption which is due to higher fat and fiber content as compared to a usual meal comprises administering an insulin dosage post-meal onset and subsequent determining the appropriate dosage. In one embodiment, insulin dosage comprises the ultra-rapid acting insulin formulation, for example, insulin-FDKP. In another embodiment, the insulin dose administration is by inhalation into the lungs using a dry powder inhaler.

Treatment of Patients of with Subcutaneous Insulin Resistance

Many of the advantages of insulin-FDKP are related to its ultra-rapid kinetics. However, insulin-FDKP is typically administered by inhalation of a dry powder preparation. There is a class of patients who can receive an additional benefit from this formulation due to its route of administration, namely patients with subcutaneous insulin resistance. This phenomenon is distinct from and unrelated to the insulin resistance typically associated with type 2 diabetes, which is generally understood to result from a reduced responsiveness of cells throughout the body to insulin.

The phenomenon of subcutaneous insulin resistance is not universally accepted by experts in diabetes as a bona fide physiological state. Certainly, its etiology is not well understood and indeed there may be multiple factors that can lead to this condition. Nonetheless experience with inhalable insulin has demonstrated the clinical reality of this phenomenon. There are patients who have required substantially greater doses of insulin than might otherwise be expected when treated with subcutaneously administered insulin who upon switching to a pulmonary insulin require an amount of insulin more in line with what would be expected based on their medical condition. Subcutaneous insulin resistance can also contribute to difficulty in establishing reasonable control of hyperglycemia and in variability in the response to insulin.

To prospectively identify diabetes patients having subcutaneous insulin resistance, several factors can be considered. First of all, the patient will be using high doses of insulin, especially compared to what would typically be required based on their medical condition including body weight and state of progression of the disease. For example, a high dose of insulin is one greater than 2 units/Kg/day. This criterion can further be paired with the patient having normal or near-normal basal levels of endogenous serum insulin, for example ≤50 µU/ml of insulin. Such patients typically will have type 2 diabetes in an early stage in the progression of the disease. Alternatively high insulin usage can be paired with lipoatrophy or lipodystrophy as diagnostic criteria.

In yet other alternative embodiments, high insulin usage can be paired with very poorly controlled hyperglycemia as the selection criteria. Very poorly controlled hyperglycemia can be evidenced by three $HbA_{1c}$ level determinations ≥9% in a 12 month period despite treatment with an intensified insulin regimen, for example basal-bolus therapy, or continuous subcutaneous insulin infusion (CSII; that is, an insulin pump), etc., over a period ≥6 months. Commonly $HbA_{1c}$ levels are determined quarterly. It is preferred that the three HbA1c level determinations ≥9% be consecutive. In alternative embodiments very poorly controlled hyperglycemia can be evidenced by two HbA1c level determinations ≥9% in a 6-9 month period.

In still further alternative embodiments, the insulin therapy that includes high insulin usage can be paired with life threatening glycemic instability as the criteria for selection. Life threatening glycemic instability can be characterized by periods of hyperglycemia and/or hypoglycemia despite adherence to diet, exercise, and insulin regimens.

Accordingly embodiments herein provide methods of treating diabetics with subcutaneous insulin resistance. These methods include a step for the selection of patients with subcutaneous insulin resistance on the basis of atypically high insulin dosage. In some embodiments the insulin dosage is ≥2 units/Kg/day. In some embodiments, the selection is further based on the patient having non-diabetic or near-normal levels of endogenous insulin. In some of these patients, the basal level endogenous insulin is ≤50 µU/ml. In other embodiments the selection is further based on the patient being on an intensified insulin regimen and having three $HbA_{1c}$ level determinations ≥9% in a 12 month period. In still other embodiments, the selection is further based on the patient having life threatening glycemic instability characterized by periods of hyperglycemia and/or hypoglycemia despite adherence to their insulin regimen and any diet or exercise regimen.

The methods also include a step of discontinuing treatment with subcutaneously administered rapid-, short-, or intermediate-acting insulin formulations; continuing injectable basal insulin therapy in patients who cannot produce sufficient insulin to meet basal requirements, and administering an initial dose prandial doses of insulin-FDKP by oral inhalation with a dry powder inhaler. Further embodiments, can include a step for confirming the diagnosis of subcutaneous insulin resistance by determining that a similar or improved degree of glycemic control is achieved with a substantially lower dosage of insulin.

In some embodiments, glycemic control is assessed by determining HbA1c level in the treated patient after a predetermined period of receiving insulin-FDKP therapy alone or in combination with other therapies. In other embodiments, the insulin therapy comprises monitoring post-prandial and/or fasting blood glucose levels to assess the efficacy of treatment. In various embodiments the insulin therapy, it has been determined that the insulin dosage (exclusive of any basal requirement) required for treatment is reduced by ≥10, ≥20, or ≥50%, or more. In some embodiments, the reduced dosage is assessed from measurements of serum insulin levels after administration based on the dosage used and the relative bioavailability of the insulin formulations.

Combined Use of Ultra-Rapid Acting Insulin and Long Acting Insulin Analogs

One mode of use of ultra-rapid acting insulin is to use it in combination with a long acting insulin in a basal-bolus regimen. In basal-bolus therapy a long acting insulin is used to provide or supplement a basal insulin level, including Lantus®, Toujeo® and Novolog®, and a bolus of short acting insulin is administered in conjunction with meals to handle the resultant increased glucose load. The various advantageous characteristics of ultra-rapid acting insulin make it an ideal choice for use as the short acting insulin in such regimens to avoid further insulin injections, especially for patients that are needlephobic.

Many long acting insulins are termed basal insulins and are administered twice a day. One basal insulin, insulin glargine (Lantus®, Sanofi-Aventis) is marketed for once a day administration. According to the manufacturer's prescribing information (March 2007 revision), insulin glargine provides relatively constant glucose lowering activity over a 24-hour period and may be administered any time during the day provided it is administered at the same time every day. Another basal insulin, insulin detemir (Levemir®, Novo Nordisk) is marketed for administration either twice a day or once a day with the evening meal or at bedtime (manufacturer's prescribing information, Version 3 issued May 16, 2007). Longer acting basal insulin with insulin action lasting about 42 hours, include, insulin degludec (Tresiba®, Novo Nodisk).

Applicants found that an ultra-rapid acting insulin formulation comprising insulin-FDKP used in combination with insulin glargine was effective in managing glucose excursions. In 7 point glucose measurements, insulin-FDKP was able to decrease the glucose levels to almost, non-diabetic, normal patterns indicating that post-prandial glucose excursions were reduced or non-existent in the treated patients (7 point graphic curve appeared almost flatten upon insulin-FDKP administration). However, over the course of the day baseline blood glucose levels tended to rise. The insulin-FDKP characteristic profile was observed in both type 1 and type 2 diabetes patients. There are several factors that may contribute to the increase in blood sugar rise during the day, one appears to be that insulin resistance tends to rise over the course of the day. Additionally, the insulin glargine used in the study was administered in the evening before bedtime as contemplated in the manufacturer's prescribing information. Thus the greatest demand for insulin activity is occurring late in the period of effectiveness of the insulin glargine dose when it is weakening during the day.

In current combination therapy, insulin glargine is used in combination with either a prandial short acting insulin, or mixes of short and intermediate acting insulins administered before breakfast and dinner. Also, intermediate acting insulins are intended to provide glucose lowering activity for both meal and between-meal periods. Even the marketed short acting insulins exert the majority of their activity after most of a meal's nutrients have been absorbed. Thus, in commonly used regimens involving combination therapy of insulin glargine and shorter acting insulins, the short acting insulin provides supplementary insulin action during waking hours. In contrast, insulin-FDKP has a short duration of action well matched to the time period in which a meal produces an excessive increase glucose level, but not providing substantial insulin activity for baseline control. Thus, in one embodiment, a basal insulin can be combined with an ultra-rapid acting insulin such as insulin-FDKP to provide any insufficiency of insulin glargine dose.

In another embodiment, a combination therapy comprises administering insulin detemir once a day in combination with insulin-FDKP at mealtime to improve glycemic control. To remediate such effects regimens combining the use of ultra-rapid acting insulins and a long acting insulin analog should specify that the long acting insulin analog be administered early in waking hours, for example at breakfast time or within 1, 2, 3 or 4 hours of waking. In some embodiments, an early dose of the long acting insulin analog is the only dose given in the course of the day. In other embodiments, the insulin therapy comprises administering a long acting insulin analog such as insulin glargine twice a day, an early morning dose and a late dose which is given approximately 8 to 14 hours later, preferably 10-12, hours later, for example, around dinnertime. In another embodiment, the insulin therapy can revolve around sleeping and waking cycles of the individual being treated.

Combined Use of Ultra-Rapid Acting Insulin and Basal Insulin Provided by Infusion Insulin pumps are compact devices that deliver various forms of insulin at appropriate times to help control the blood glucose level. Used correctly, these devices improve blood glucose control with fewer hypoglycemic episodes and better long-term control. The pumps are programmable and give patients a degree of freedom to vary what, when or how much they eat by allowing insulin delivery rates to be adjusted for different times of day. The latest models of insulin pumps are relatively easy to use and convenient to carry. These newer pumps have built-in dosage calculators that manage the complex insulin dosage calculations previously performed by patients. Patients are able to program bolus doses to coincide with a meal as well as different basal insulin delivery rates for different times of day, depending on changing needs. These pumps also calculate how much insulin is still working from the previous bolus dose. Some pumps have additional smart features such as programmable reminders and alerts, information and download capabilities that allow the patient to save information to a computer for accurate record-keeping, a carbohydrate database for calculating the amount of carbohydrate ingested in a meal, and certain safety features.

As an alternative to subcutaneous bolus injection of long acting insulin, it is also possible to provide basal insulin by continuous infusion. This approach obviates the need for long acting insulin since insulin is continually provided. This approach can also avoid any drawbacks associated with such preparations, for example increased immunogenicity or binding to receptors for insulin-like growth factors that can occur with analogs. As the rate of infusion can be changed throughout the day with this approach, the profile of basal insulin activity can be more readily adjusted to variations in diet and individual physiology. (The capabilities of insulin pumps are more fully discussed in the section dealing with artificial pancreas systems, below). A common methodology with insulin pumps is to aim to cover both prandial and basal needs by using one of the rapid acting analogs. When the pump is only being used to provide basal insulin—as with a prandial non-pumped ultra-rapid acting insulin—regular human insulin can be used. However for patients with less stable basal need the more rapid kinetics of the rapid acting analogs can offer an advantage.

In an alternate embodiment, the insulin therapy comprises a method of treating diabetes comprising, infusing insulin with an insulin pump to a patient in need thereof to meet basal insulin needs and, administering an ultra-rapid acting insulin at mealtime to meet prandial needs. In some embodiments, the pumped insulin is regular human insulin, or a rapid acting insulin analog. In one embodiment, the ultra-rapid acting insulin formulation is insulin-FDKP, which is administered by inhalation into the lungs at mealtime Use of Ultra-Rapid Acting Insulin in Combination with or in Place of Oral Antidiabetic Medications Standard of care in the treatment of type 2 diabetes is defined and regularly updated in consensus statements published jointly by the American Diabetes Association and the European Association for the Study of Diabetes. The general course of treatment advocated, summarized below, has remained fairly stable in recent years (compare for example Nathan et al. Diabetes Care 29:1963-1972, 2006; Nathan et al. Diabetes Care 31:173-175, 2008; and Nathan et al. Diabetes Care 32:193-203, 2009) with the most significant change in the most recent update being the addition of GLP-1 agonists to the treatment algorithm.

The course of treatment as advocated in these consensus statements begins with lifestyle changes plus the drug metformin at diagnosis (Step 1). Lifestyle changes include improved diet and increased exercise. Metformin is a drug classified as a biguanide. Although historically these drugs have been described as insulin sensitizers, their primary effect is to reduce hepatic glucose output. This activity appears to be dependent on the presence of insulin and metformin treatment can be associated with somewhat increased sensitivity to insulin. However, avoided herein is applying the term "insulin sensitizer" to the biguanides as the mechanism of action is different from that of the thiazolidinediones which are now more commonly intended by the term and for which the primary effect to increase insulin sensitivity. As metformin is present throughout the day its effect is observed as a reduction in fasting blood glucose levels (FBG). Approximately 30% of patients cannot tolerate metformin, at least at dosages adequate for acceptable glycemic control, with gastrointestinal side-effects being a primary issue. The prescribing information (January 2009 revision) for metformin (Glucophage®, Bristol-Myers Squibb) includes contraindications for use in patients with renal disease or dysfunction, hypersensitivity to the drug, or metabolic acidosis, as well as other precautions.

If adequate glycemic control is not attained (generally HbA1c remains ≥7%) with Step 1 treatment, Step 2 treatment calls for the addition of a second therapy. This can be basal insulin, a sulfonylurea, pioglitazone, or a GLP-1 agonist. If the two agents (the second agent not being basal insulin) still do not establish adequate glycemic control the consensus calls for either switching the second agent to basal insulin, or using a combination therapy of a sulfonylurea and pioglitazone as the second agent. If the combination of a sulfonylurea and pioglitazone still does establish adequate glycemic control the consensus calls for switching the second agent to basal insulin. By any of these paths the consensus advocates that the first insulin regimen used be basal insulin.

The sulfonylureas are insulin secretagogues, that is, they enhance insulin secretion. Included in this class are the drugs chlorpropamide, glyburide, gliclazide, glimepiride and glipizide. A major issue with these agents is an increased risk of hypoglycemia, especially great with chlorpropamide and glyburide. Use of these agents has also been implicated in increased mortality from cardiovascular disease and weight gain. Contraindications, precautions, and drug interactions typical of the sulfonylureas can be found in the prescribing information for glipizide (Glucotrol®, Pfizer) and concern has also been raised that insulin secretagogues increase demand on an already overtaxed pancreas, contributing to the progressive decrease in β-cell function and limiting their long term usefulness, including, the glinides, for example, repaglinide and nateglinide. The risk of weight gain with these agents is similar to the sulfonylureas, but the risk of hypoglycemia may not be as elevated. GLP-1 agonists and DPP-4 (dipeptidyl peptidase-4) inhibitors can also be considered insulin secretagogues. As used, insulin secretagogues provide their activity throughout the day so that their effect is readily seen as a reduction in fasting blood glucose.

Pioglitazone such as Actos® (Takeda Pharmaceuticals) is a thiazolidinedione (glitazone, TZD) which increase the sensitivity of muscle, fat, and liver to insulin, thereby counteracting the insulin resistance aspect of type 2 diabetes, and are therefore commonly referred to as insulin sensitizers. TZDs have been associated with fluid retention and congestive heart failure and also with increased rates of bone fracture, especially in women with osteoporosis. The TZDs also include the drug rosiglitazone such as Avandia® (GlaxoSmithKline) which has been further associated with myocardial ischemia. These and other side-effects, precautions, etc., such as weight gain are reporting in the manufacturer's prescribing information for Actos® (August 2008 version) and Avandia® (October 2008 version) can be decreased using the present formulations.

Patient populations treated according to the embodiments herein disclosed are distinct from those most commonly receiving insulin therapies. The factors that might impel a clinician to prescribe insulin to individuals according to current paradigms do not shed any light on the relative effectiveness of an ultra-rapid acting insulin as compared to oral antidiabetic agents especially given the distinct pharmacokinetic profiles of the insulin preparations available. Moreover, as seen above use of insulin typically begins with basal insulin, with prandial insulins being added only after the failure of basal insulin alone. In contrast, the methods disclosed herein involve use of prandial ultra-rapid acting insulin early in the progression of treatment.

Patients with early stage insulin disorders can be divided into various subpopulations and treated according to various embodiments of the present invention. Some individuals make sufficient insulin to maintain a non-hyperglycemic fasting blood glucose level but cannot avoid acute fluctuations in blood glucose after eating. Early type 2 diabetics can often use diet and exercise to control even substantial hyperglycemia, but may have already lost their early phase insulin release. In current practice, patients failing diet and exercise are most often next treated with a suppressor of hepatic glucose output, such as metformin, with the goal of overcoming insulin resistance and improving the effectiveness of the insulin that is endogenously produced by the pancreas.

In embodiments disclosed herein, these patients are administered a prandial, early phase-mimicking insulin preparation instead of, or in addition to, the insulin sensitizer. Less often (and previously) the first oral medication offered diabetics was an insulin secretagogue, such as a sulfonylurea, to increase insulin secretion. More commonly (and currently) such agents are used in combination with a suppressor of hepatic glucose output as a subsequent step in treatment if use of the sensitizer alone does not provide the desired level of glycemic control. However, use of secretagogues can also lead to weight gain and hypoglycemic events. Therefore, in a one embodiment, a prandial, ultrarapid insulin therapy comprising an early phase-mimicking insulin preparation is used to replace an insulin secretagogue in such combination treatments.

Both fasting and postprandial blood glucose levels contribute to elevation of HbA1c levels. Ultra-rapid acting insulin preparations can advantageously impact both fasting and postprandial blood glucose levels. Accordingly, a method for controlling postprandial blood glucose is provided wherein insulin-FDKP is administered to replace basal insulin or insulin secretagogues, or even short acting insulins in type 2 diabetes treatment. This is understood to be due in part to their more rapid suppression of endogenous glucose production (see Example 1). Thus embodiments disclosed herein are directed to patients with poorly controlled postprandial blood glucose or in whom the lack of glycemic control, which is more strongly associated with elevated postprandial blood glucose. For example, patients with a lesser degree of insulin resistance may be able to produce sufficient insulin to provide substantial control of fasting blood glucose, and in some embodiments can be selected for treatment with ultra-rapid insulin alone. In comparison, patients with a higher degree of insulin resistance may have poor control of both fasting and postprandial blood glucose and in this scenario, the therapy comprises a treatment with ultra-rapid insulin and an oral antidiabetic agent in combination.

Ultra-Rapid Acting Insulin and Suppressors of Hepatic Glucose Output

Both ultra-rapid acting insulin and biguanide drugs such as metformin act as suppressors of hepatic glucose release. However, as used, the drugs exert their effect continuously throughout the day, whereas prandial ultra-rapid acting insulin exerts this effect more particularly following meals. Thus, ultra-rapid acting insulin can substitute for or augment the activity of the oral suppressors of hepatic glucose output.

Accordingly, in one embodiment ultra-rapid acting insulin is used in treating a subject with type 2 diabetes in need of improved glycemic control with well or moderately controlled fasting blood glucose levels, but poorly controlled PPG, wherein the therapy comprises improving glycemic control as determined by HbA1c level, detecting 1- or 2-hour PPG levels, and/or oxidative stress. In some embodiments, well controlled FBG is FBG ≤110 or ≤130 mg/dL. In some embodiments, a moderately controlled FBG is FBG ≤154 mg/dL, ≤180, or ≤192 mg/dL. Studies have determined that at HbA1c levels ≤8.4% at least half of overall hyperglycemia is due to PPG (Monnier, L. et al. Diabetes Care 26:881-885, 2003). Thus in some embodiments, a subject with well or moderately controlled FBG, but poorly controlled PPG is a subject with HbA1c ≤8.4%. (An HbA1c of 8.4% corresponds to a mean plasma glucose level of approximately 192-198 mg/dL; see Diabetes Care 32, suppl.1:S13-561, 2009, especially tables 8 and 9). In various embodiments, a subject with poorly controlled PPG is one with 1- or 2-hour PPG ≥140, or ≥180, or ≥200 mg/dL. It should be noted that subjects whose 2-hour PPG following a 75 g glucose challenge was ≥200 mg/dL had an almost doubled risk of mortality than those whose 2-hour PPG was ≤200 mg/dL regardless of their FPG (Lancet 354:617-621, 1999). In one embodiment, the insulin therapy includes a subject which is not currently receiving any drug treatment; and ultra-rapid insulin is administered to the subject as the sole pharmacologic agent. In another embodiment, the subject is undergoing treatment with an oral suppressors of hepatic glucose output and prandial ultra-rapid insulin is added to the treatment regimen. In one embodiment, the therapy includes oral suppressors of hepatic glucose output, which can be metformin. In these embodiments, the ultra-rapid acting insulin formulation is insulin-FDKP.

In other embodiments, a subject with type 2 diabetes in need of improved glycemic control could benefit from treatment with a suppressor of hepatic glucose output, but if such oral agents are contraindicated or not tolerated, and ultra-rapid acting insulin is used instead. In a variation of the therapy, the oral agent is not tolerated in sufficient dosage and ultra-rapid acting insulin is used to supplement its activity.

Ultra-Rapid Acting Insulin and Insulin Secretagogues

Insulin secretagogues such as the sulfonylureas and the glinides increase insulin secretion and thereby insulin concentrations in circulation. Ultra-rapid acting insulin preparations also increase insulin concentrations in circulation. However, therapy with glinides, the drugs exert their effect continuously throughout the day, whereas prandial ultra-rapid acting insulin exerts this effect more particularly following administration with meals. Thus, in one aspect of diabetes treatment, an ultra-rapid acting insulin can substitute for the activity of the insulin secretagogue. In one embodiment, a method of treating type 2 diabetes comprises administering an ultra-rapid acting insulin formulation including insulin-FDKP to a patient in need by oral inhalation into the lungs using a dry powder inhaler. In one embodiment, a subject with type 2 diabetes can improve glycemic control and who is receiving oral agents which are contraindicated or not well-tolerated, by adding or replacing the oral agents with an ultra-rapid acting insulin and reducing the risk of hypoglycemia or weight gain.

Ultra-Rapid Acting Insulin and Insulin Sensitizers

Insulin sensitizers, such as pioglitazone and the other TZDs improve insulin utilization in various tissues thereby reducing insulin resistance and leading to a reduction in circulating insulin levels. Treatment with TZDs results in notable decreases in FBG. Treatment with prandial ultra-rapid acting insulin leads to a reduction in FBG. This is despite the fact that there is no direct glucose eliminating activity due to prandial ultra-rapid acting insulin during fasting periods. The impact of ultra-rapid acting insulin preparations on fasting blood glucose levels was unexpected and suggests that they can reduce insulin resistance or act as an insulin sensitizer. The rapid insulin concentration peak obtained with ultra-rapid acting potentiates subsequent insulin activity. This is particularly noticeable in type 2 diabetics in the time frame immediately following administration, however, the effect may be longer lived.

Thus, in one embodiment, the method comprises a combination therapy treatment comprising prandial ultra-rapid acting insulin which additionally acts as an insulin sensitizers. In one embodiment, patients are selected for treatment comprising an ultra-rapid acting insulin on the basis of having a high degree of insulin resistance and who would benefit from treatment with an insulin sensitizer, such as a TZD, but have a sensitivity to the drug or are otherwise contraindicated for TDZ treatment, for example, women with osteoporosis, and instead patients are treated with an ultra-rapid acting insulin in place of the drug.

Patients who can benefit from treatment with prandial ultra-rapid acting insulin according to various embodiments include those who obtain inadequate glycemic control with an insulin sensitizer and would otherwise have an insulin secretagogue added to their treatment regimen, or those who obtain inadequate glycemic control with a combination of an insulin sensitizer and an insulin secretagogue. Subsets of these groups include those who further are needle-phobic or would otherwise want to avoid injections, and those who further are obese, overweight, or otherwise desire to avoid or minimize weight gain or need to lose weight. Additionally, elevated insulin levels are associated with a greater occurrence of breast cancer. Thus persons with an elevated risk of breast cancer can particularly benefit from lowering their insulin resistance by replacing or adding an ultra-rapid-acting insulin formulation such as insulin-FDKP to their diabetes therapy to minimize these risks.

Prandial Ultra-Rapid Insulin Versus Basal Insulin

When treatment with two oral medications does not provide adequate glycemic control standard of care offers paths to the use of basal insulin or use of a third oral medication. The choice to add a third oral medication instead of adding insulin is often influenced by reticence to accept daily injections even in the absence of an outright needle phobia, the risk of hypoglycemia, and the likelihood of weight gain. Thus embodiments of the invention provide a successor treatment to combination oral therapy that includes insulin, but is needle-free and minimizes or eliminates weight gain. The inhalable insulin Exubera®, because of its subcutaneously delivered insulin-like kinetics, would not be expected to confer the same benefits as an ultra-rapid acting insulin preparation. This use shows that prandial ultra-rapid insulin offers a unique alternative to the early use of basal insulin generally, and that offers particular advantage to patient populations in which needle use, the risk of hypoglycemia, or the prospect of weight gain are particularly problematic.

Patients who can benefit from treatment according to various embodiments disclosed herein include those who obtain inadequate glycemic control with an oral suppressors of hepatic glucose output and would otherwise have an insulin secretagogue added to their treatment regimen, or those who obtain inadequate glycemic control with a combination of an oral suppressor of hepatic glucose output and an insulin secretagogue. Subsets of these groups include those who further are needle-phobic or would otherwise want to avoid injections, and those who further are obese, overweight, or otherwise desire to avoid weight gain or need to lose weight Example 1

Study Design and Methods:

The study was conducted to monitor postprandial glucose excursions in insulin-requiring diabetes mellitus patients. Two types of insulins were used for treating Type 1 patients: an instant ultrarapid rapid-acting insulin (Technosphere insulin-TI, dry powder inhalable recombinant human insulin) and commercially available rapid acting insulin analog, insulin aspart, Novolog® administered by subcutatneous injection was used as the comparator. All patients in the study received a basal insulin once a day in the morning and a cohort group was treated at each of their mealtime with insulin glargine, Lantus® and either TI, and another cohort group received the rapid acting insulin analog, insulin aspart, Novolog®. Individuals were randomized to either titrated insulin aspart as standard protocol. All patients were instructed to take their insulins at each mealtime with their regular meals, and to monitor their glucose levels at various predetermined times at least at 1 and 2 hours after mealtime. Blood glucose levels were monitored at various time points after administration. Patients in taking insuli Applicants performed a detailed, post hoc regression analysis to evaluate overall and severe hypoglycemic event rates based on the HbA1c level achieved in patients treated with an inhalable ultra-rapid acting insulin versus subcutaneously administered insulin aspart (Novolog®). Inhalable ultra-rapid acting insulin was prepared and used in this experiments at 4 units, 8 units, 12 units, 16 units, 20 units and 24 units of insulin per dose. Supplemental doses could be taken at 90 minutes after the mealtime dose if blood sugar levels were greater than 140 mg/dL Post hoc analysis was performed on a representative subset of the AFFINITY 1 (24-week treat-to-target study in T1D: NCT01445951, MannKind Corporation) cohort for whom an end-of-treatment value for HbA1c was known. The results are shown in Table 1.

TABLE 1

Population Comparison:
Original vs Post Hoc Analysis

| Mean HbA$_{1c}$ (%) | Insulin aspart | TI | Treatment difference |
|---|---|---|---|
| Original analysis (MMRM) | | | |
| N | 170 | 174 | |
| Baseline | 7.92 | 7.94 | |
| End of treatment | 7.52 | 7.73 | |
| Adjusted mean change | −0.40 | −0.21 | 0.19 |
| 95% Cl | −0.52, −0.28 | −0.33, −0.09 | 0.02, 0.36 |
| Post hoc analysis (AVCOVA) | | | |
| N | 147* | 129 | |
| Baseline | 7.88 | 7.97 | |
| End of treatment | 7.47 | 7.76 | |
| Mean change | −0.40 | −0.21 | 0.20 |
| 95% Cl | −0.53, −0.28 | −0.34, −0.08 | 0.02, 0.38 |

Figure 2:
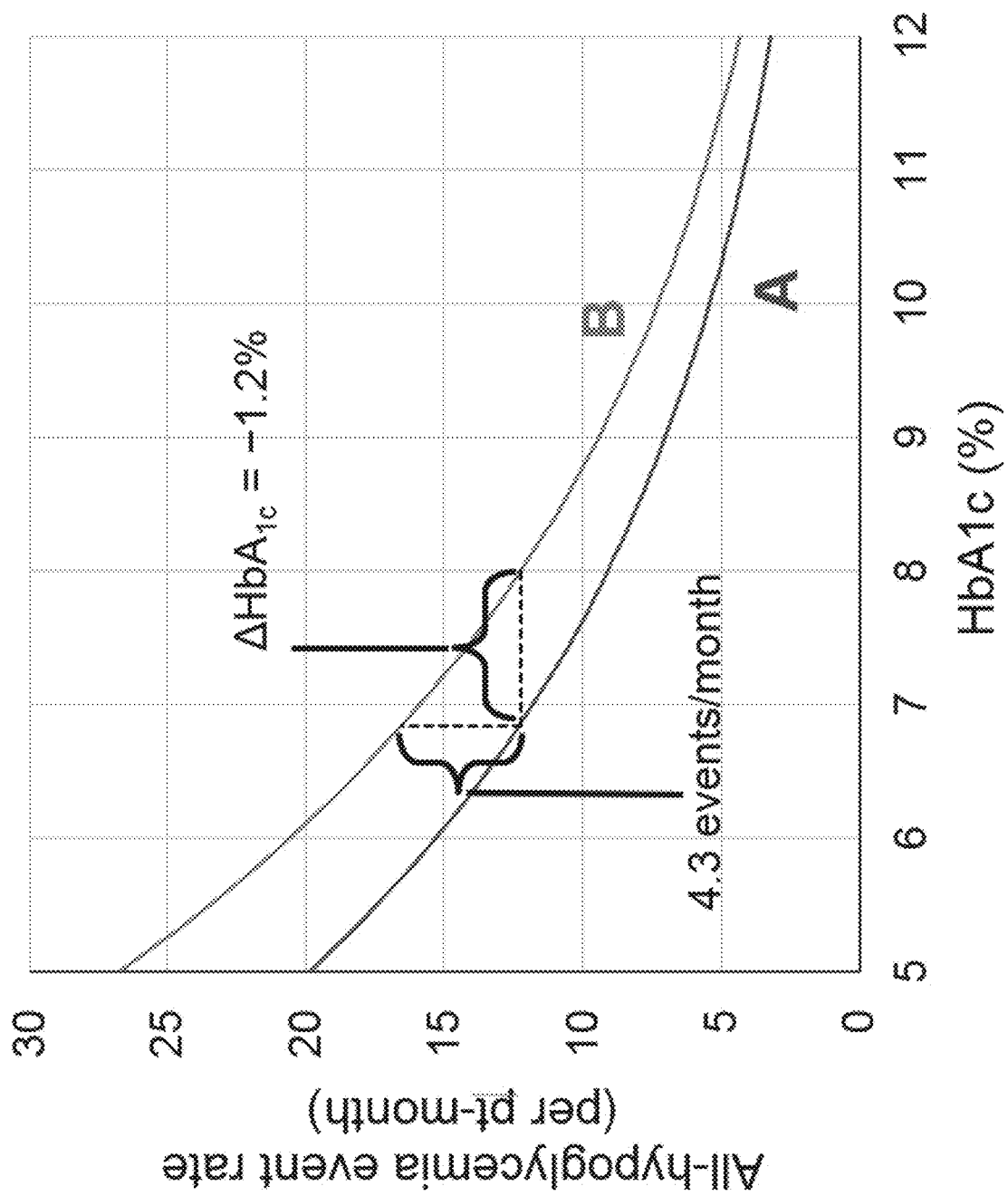
FIG. 2 depicts a graphic representation of data obtained from clinical studies of patients treated with the instant ultra-rapid acting insulin (TI, line A) compared to a rapid acting insulin analog, insulin aspart (line B), demonstrating a comparison of estimated hypoglycemia rates versus achieved $HbA_{1c}$.

In this analysis, hypoglycemia was defined as any self-monitored blood glucose <70 mg/dL or symptomatic events that corrected with carbohydrate ingestion. Severe hypoglycemia was defined in the usual fashion and as defined herein above. Frequency of hypoglycemia was modeled as a negative binomial distribution with mean μ and reciprocal dispersion factor ν. The logarithm of μ, ln (μ), was modeled as a linear function of the continuous variable HbA1c and indicator variables representing treatment, basal insulin, and region (FIG. 1). As shown in FIG. 1, use of TI versus aspart was associated with significantly lower rates of hypoglycemia. At any given HbA$_{1c}$ level, overall rates of hypoglycemia with TI were reduced ~26% to about 30%. Achieved HbA$_{1c}$ does not account for the differences observed in hypoglycemia. As seen in the triangle in the graph in FIG. 2, the horizontal line (change in HBA$_{1c}$) shows the difference between the two treatments, i.e., was equal to 1.2% between treatment with insulin aspart (curve B) and TI (curve A). FIG. 2 also depicts the difference between in hypoglycemia events between insulin aspart and TI treatment, which indicate that there were 4.3 hypoglycemic events/month less with TI treatment.

Moreover, hypoglycemia incidence and events were tabulated and evaluated using $\chi 2$ statistics and are presented in Table 2.

As shown in Table 2, patients treated with the instant ultra-rapid acting insulin (TI) had significantly less hypoglycemic events than those patients treated with insulin aspart.

TABLE 2

Summary of Hypoglycemia Incidence And Events

| | Parameter | Aspart | TI | P value |
|---|---|---|---|---|
| | N | 150 | 129 | |
| All hypoglycemia | Incidence, n (%) | 150 (100) | 129 (100) | 1 |
| | Events | 11,723 | 6983 | <0.001 |
| | Events per patient | 78.2 | 54.1 | |
| Severe hypoglycemia | Incidence, n (%) | 47 (31.3) | 28 (21.7) | 0.071 |
| | Events | 127 | 59 | 0.114 |
| | Events per patient reporting at least 1 severe hypoglycemic event | 2.7 | 2.1 | |

Moreover, ultra-rapid acting insulin (TI) allows for greater HbA$_{1c}$ reduction with lower rates of hypoglycemia as shown in FIG. 2. The resultant analysis shows that HbA$_{1c}$ could be reduced by 1.2% at a hypoglycemia rate of 12.2 events/month with TI and the total events could be reduced by 4 per patient-month at an HbA$_{1c}$ of ~6.8%.

FIG. 3A-3F depicts data illustrating postprandial glucose excursion profiles across TI-treated/insulin aspart dose ratios for patients in this study. In FIG. 3A are data obtained from 49 patients treated with basal insulin (insulin glargine) and insulin aspart as the mealtime insulin, and 97 patients received the same basal insulin and 4 units of TI. In FIGS. 3B, 3C, 3D, 3E and 3F, the study was conducted similarly, except the units of insulin were increased, respectively, 8 units (210 patients), 12 units (103 patients), 16 (134 patients), 20 (36 patients) and 24 (63 patients) for TI and 4±1 units (120 patients), 6±1 (208 patients), 8±1 (137 patients), 10±1 (134 patients) and 12±1 (96 patients) for insulin aspart, respectively.

The data in FIGS. 3A-3F indicate that both treatments were good at controlling glycemia at lower dosage levels. However, TI treatment resulted in significantly lower rates of hypoglycemia at higher dose levels.

Figure 4A:
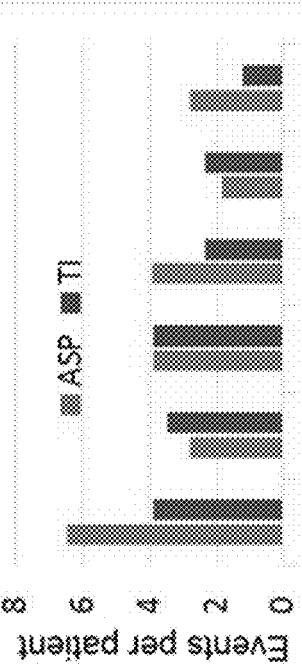
FIG. 4A-4D depict hypoglymic events in the postprandial period following a meal of patients as treated in the study in FIG. 3. The data from the study in FIG. 3A-3F shows the hypoglycemic events per patient in insulin aspart treated (gray bars) Type 1 diabetes patients and patients treated with an ultra-rapid inhaled insulin, TI (solid/black bar) for various doses administered monitored for 0-2 hrs after mealtime and 2-4 hrs after mealtime.
Figure 4C:
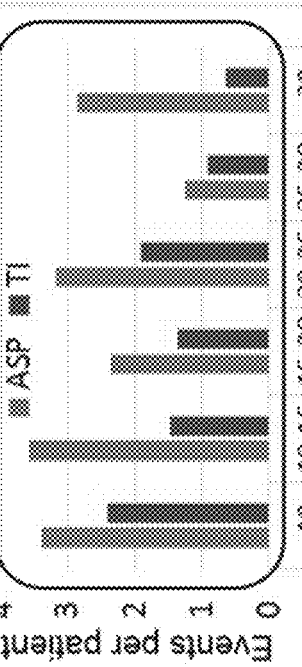
Figure 4B:
Figure 4D:
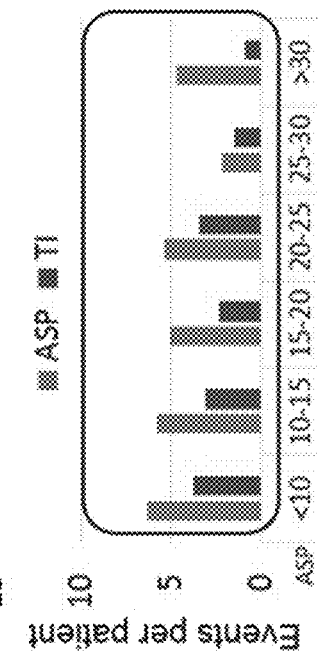

FIGS. 4A, 4B, 4C and 4D depict data from patients treated with a combination therapy comprising Lantus® as the basal insulin and either insulin aspart (gray bars) or insulin-FDKP (TI, solid black bars) as the prandial/mealtime insulin as described above. Patients were educated on how to take their dosages and told to go home and take their dosages with their meals. The number of prandial insulin units was predetermined and illustrated in the figure. FIGS. 4A-4B show bar graphs of the patients treated illustrating the number of hypoglycemic events experience by the patients receiving various amounts of insulin units which wherein the inhalation units for TI were calculated to substantially be equivalent to the subcutaneous insulin units tested. FIGS. 4A and 4B depicts the results of all hypoglycemic events recorded by all patients in the treatment. The hypoglycemic events were noted up to 2 hours (FIG. 4A, 4C) and from 2-4 hours (FIG. 4B, 4D) after treatment. FIGS. 4C and 4D depict the data for patients who reported level 2 hypoglycemia, which is moderate episodes. The data show that treatment with TI resulted in less hypoglycemic events per patient in all doses tested and that there was a higher rate of late post-meal hypoglycemia across all insulin doses. The time in hypoglycemia for all patients was also tested and the results show the patients who experienced a shorter time in hypoglycemia were those patients receiving TI, wherein the hypoglycemic episodes were of shorter duration.

The data analysis from the trials demonstrate that the use of the ultra-rapid-acting inhaled insulin (TI) significantly lowers the rate of hypoglycemia in type 1 diabetes while providing noninferior glycemic control. The data also show that the use of TI in a multi-dose insulin regimen may permit treatment intensification to be achieved with less hypoglycemia and that switching to an inhaled ultra-rapid regimen may also benefit patients already at HBA1c goal by reducing the frequency of hypoglycemic events.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments disclosed herein are illustrative of the principles of the present invention. Other modifications that may be employed are within the scope of the invention. Thus, by way of example, but not of limitation, alternative configurations may be utilized in accordance with the teachings herein. Accordingly, the present invention is not limited to that precisely as shown and described.

We claim:

1. A method of treating diabetes comprising, administering to a patient with diabetes, exhibiting hypoglycemic events, a pharmaceutical composition comprising an inhalable dry powder comprising insulin and fumaryl diketopiperazine to replace rapid acting insulin analog used at mealtime, wherein the patient is not taking basal insulin and the pharmaceutical composition upon inhalation mimics native insulin release during a meal and significantly reduces the rate of hypoglycemic events in the patient who is subject to severe hypoglycemia with rapid acting insulin analog treatment.

2. The method of claim 1, wherein the pharmaceutical composition comprises human recombinant insulin.

3. The method of claim 1, wherein the pharmaceutical composition comprises fumaryl diketopiperazine which comprises crystalline particles.

4. The method of claim 1, wherein the pharmaceutical composition comprises a dry powder, which comprises 4 units, 8 units, 12 units, 16 units, 20 units, 24 units, or 30 units of a recombinant human insulin per dose administered.

5. The method of claim 1, wherein the pharmaceutical composition comprises a dry powder which is in substantially crystalline form.

6. The method of claim 1, wherein the inhalable dry powder is administered to a patient in need of treatment by oral inhalation using a dry powder inhaler.

7. The method of claim 6, wherein the dry powder is administered in at least one inhalation in less than 4 seconds per dose.

8. The method of claim 1, further administering a supplemental dose of the inhalable dry powder by oral inhalation if blood glucose levels are greater than 140 mg/dL 2 hours after eating a meal.

9. The method of claim 8, wherein the supplemental dose comprises up to 30 units of insulin.

10. The method of claim 1, wherein the patient with diabetes is a type 1 patient and the dry powder pharmaceutical composition is administered in a combination therapy with a basal insulin.

11. The method of claim 10, wherein the basal insulin is insulin glargine, insulin aspart or insulin degludec.

12. The method of claim 1, wherein the hypoglycemic events are reduced by about 30% when compared with patients receiving a rapid acting insulin analog therapy by injection.

* * * * *